United States Patent [19]
Kawaguchi et al.

[11] Patent Number: 6,022,998
[45] Date of Patent: Feb. 8, 2000

[54] STILBENE DERIVATIVE AND METHOD FOR PRODUCING THE SAME

[75] Inventors: Hirofumi Kawaguchi; Yukimasa Watanabe; Yoshio Inagaki, all of Osaka, Japan

[73] Assignee: Mita Industrial Co., Ltd., Osaka, Japan

[21] Appl. No.: 09/118,834

[22] Filed: Jul. 20, 1998

[30] Foreign Application Priority Data

Jul. 24, 1997 [JP] Japan .................................. 9-198723

[51] Int. Cl.$^7$ .................................................. C07C 211/00
[52] U.S. Cl. ................................ 564/434; 430/72; 430/73
[58] Field of Search ............................... 564/434; 430/73, 430/72

[56] References Cited

FOREIGN PATENT DOCUMENTS 50-31773   3/1975   Japan .
7-244389   9/1995   Japan .

OTHER PUBLICATIONS

Suzuki et al. (CA113:221304f); JP 02, 109,056, Apr. 1990.

*Primary Examiner*—Samuel Barts
*Attorney, Agent, or Firm*—Smith, Gambrell & Russell

[57] ABSTRACT

The present invention provides a novel stilbene derivative represented by the general formula (1):

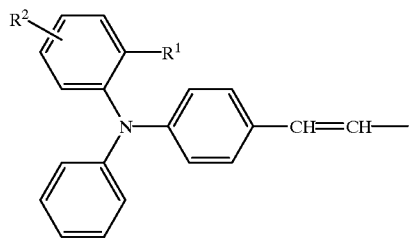

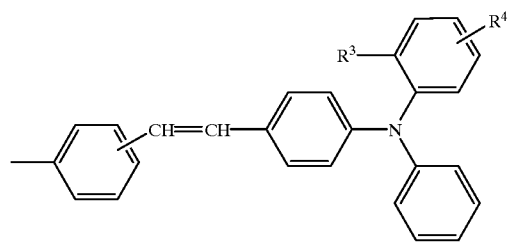

wherein $R^1$ and $R^3$ represent an alkyl group, an aryl group, an aralkyl group or an alkoxy group which are optionally substituted; and $R^2$ and $R^4$ represent a hydrogen atom, an alkyl group or an alkoxy group which are optionally substituted, provided that when the substitution position of $R^2$ and $R^4$ is the 4-(para) position, $R^2$ and $R^4$ are hydrogen atoms, a method for producing the same and use thereof. The above stilbene derivative (1) is useful as an electric charge transferring material, particularly hole transferring material.

30 Claims, 8 Drawing Sheets

STILBENE DERIVATIVE AND METHOD FOR PRODUCING THE SAME

BACKGROUND OF THE INVENTION

The present invention relates to a novel stilbene derivative which is suitably used as an electron charge transferring material (particularly hole transferring material) in a solar battery, an electroluminescence device, an electrophotosensitive material or the like, and a method for producing the same.

In image forming devices, various photoconductors having a sensitivity at the wavelength range of a light source used in said devices have been used. The organic photoconductor has widely been used because of its advantages such as easy production in comparison with a conventional inorganic photoconductor, various selective photosensitive materials (e.g. electric charge transferring material, electric charge generating material, binding resin, etc.) and high functional design freedom.

Examples of the organic photoconductor include a single-layer type photoconductor wherein an electric charge transferring material and an electric charge generating material are dispersed in the same photosensitive layer, and a multi-layer type photoconductor comprising an electric charge generating layer containing an electric charge generating material and an electric charge transferring layer containing an electric charge transferring material, which are mutually laminated.

As the electric charge transferring material used in the above photoconductor, a stilbene derivative is disclosed in Japanese Patent Laid-Open Publication Nos. 50-31773 and 7-244389.

However, since the stilbene derivative disclosed in the above patent publications is normally inferior in compatibility with a binding resin and is not uniformly dispersed in the photosensitive layer, electric charges hardly move. Therefore, although the above stilbene derivative itself has high electric charge mobility, when using this stilbene derivative as an electric charge transferring material, the characteristics can not be sufficiently exerted. Accordingly, the residual potential of the photoconductor becomes higher and the photosensitivity was not sufficient.

SUMMARY OF THE INVENTION

It is a main object of the present invention to solve the above technical problems, thereby to provide a novel stilbene derivative which is suitable as an electric charge transferring material of an electrophotosensitive material, and to provide a method for producing the same.

It is another object of the present invention to provide an electrophotosensitive material whose sensitivity is improved in comparison with a conventional one.

The present inventors have studied intensively in order to solve the above problems. As a result, the present inventors have found a new fact that, among stilbene derivatives, a compound whose diphenylamino groups at the molecular end is unsymmetrical, particularly a stilbene derivative represented by the following general formula (1), wherein one phenyl group in the above diphenylamino group has no substituent and the other phenyl group has a substituent at the 2- and 3-position, 2- and 5-position, 2- and 6-position or only at the 2-position, is superior in compatibility with a binding resin to a conventional stilbene derivative and has large electric charge mobility. Thus, the present invention has been accomplished.

General formula (1):

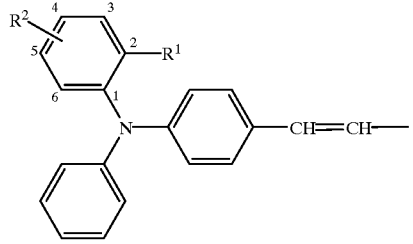

(1)

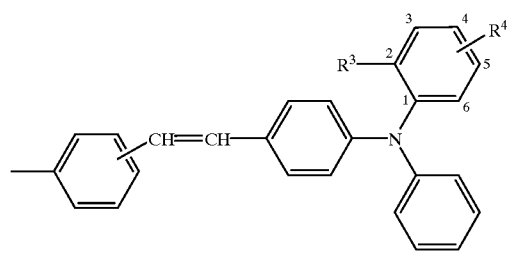

(wherein $R^1$ and $R^3$ are the same or different and represent an alkyl group, an aryl group, an aralkyl group or an alkoxy group which are optionally substituted; and $R^2$ and $R^4$ are the same or different and represent a hydrogen atom, an alkyl group or an alkoxy group which are optionally substituted, provided that when the substitution position of $R^2$ and $R^4$ is the 4 (para)-position, $R^2$ and $R^4$ are hydrogen atoms)

The stilbene derivative represented by the above general formula (1) is a compound, which is not specifically disclosed in Japanese Patent Laid-Open Publication Nos. 7-244389 and 50-31773, and has high compatibility with a binding resin in comparison with a compound disclosed in the above patent publications and has large electric charge mobility. Therefore, a high-sensitivity electrophotosensitive material can be provided by using such a stilbene derivative (1) as an electric charge (hole) transferring material in the electrophotosensitive material.

Furthermore, the present inventors have intensively studied about the method of efficiently obtaining the following formyl compound (2) of triphenylamine:

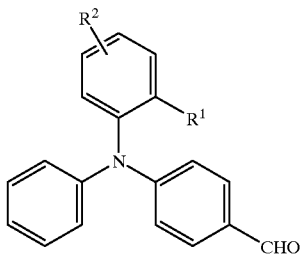

(2)

(wherein $R^1$ and $R^2$ are as defined above) as a starting material in the method of producing the above stilbene derivative (1). As a result, the present inventors have found that, when a triphenylamine derivative (5):

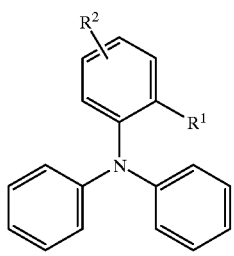

(5)

(wherein R[1] and R[2] are as defined above) having a substituent at the 2-position of a phenyl group is formulated by the Vilsmeier method, the above compound (2), wherein the phenyl group having a substituent among three phenyl groups of the compound (5) is not formulated and only non-substituted phenyl group of the compound (5) is formulated, can be efficiently produced, resulting in improvement of the productivity of the stilbene derivative (1). Thus, the present invention has been accomplished.

That is, the method of producing the stilbene derivative (1) of the present invention is characterized by reacting a formulated triphenylamine derivative represented by the general formula (2):

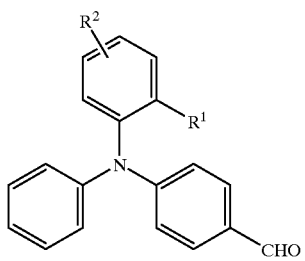

(2)

(wherein R[1] and R[2] are as defined above) with a bisphosphate derivative represented by the general formula (3):

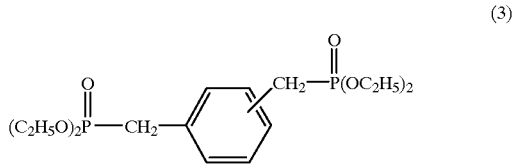

(3)

The above formylated triphenylamine derivative (2) used in the production method of the present invention is a compound obtained by reacting an aniline derivative represented by the general formula (4):

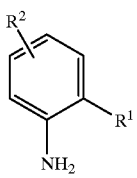

(4)

(wherein R[1] and R[2] are as defined above) with iodobenzene to obtain a triphenylamine derivative represented by the general formula (5):

(5)

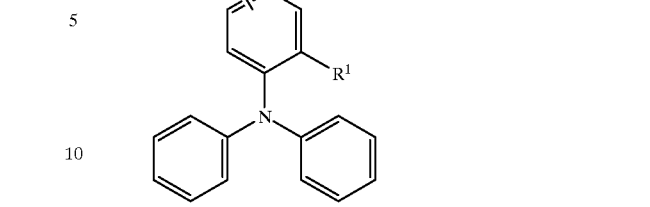

(wherein R[1] and R[2] are as defined above) and formulating this compound (5) by the Vilsmeier method.

When the above triphenylamine derivative (5) is formulated by the Vilsmeier method, only the formyl compound (2) of triphenylamine as the raw material of the stilbene derivative (1) is produced in high yield. The reason is not sure. Regarding the phenyl group having a substituent R[1] at the ortho-position among three phenyl groups of the above compound (5), a bonding axis of a nitrogen atom and a phenyl group in the above compound (5) causes distortion by an influence of the substituent R[1] and donation of electrons from the nitrogen atom is lowered, which results in deterioration of nucleophilicity of the phenyl group. As a result, the para-position of the phenyl group is not formulated and only the para-position of the other phenyl group is formulated.

The electrophotosensitive material of the present invention is an electrophotosensitive material comprising a conductive substrate, and a photosensitive layer provided on the conductive substrate, characterized in that the photosensitive layer contains a stilbene derivative represented by the above general formula (1).

Since the electrophotosensitive material of the present invention contains the stilbene derivative represented by the above general formula (1) in the photosensitive layer, the rate of transferring electric charges (holes) generated in the electric charge generating material is fast, that is, the electric charge mobility is large and the photosensitivity at the time of charging and exposure is excellent. As a result, according to the electrophotosensitive material of the present invention, high sensitivity can be obtained in comparison with the case where a conventional stilbene derivative is used as a hole transferring material.

The photosensitive layer is preferably a single-layer type photosensitive layer containing an electric charge generating material and an electron transferring material, together with the stilbene derivative represented by the above general formula (1).

DETAILED DESCRIPTION OF THE INVENTION

Figure 1:
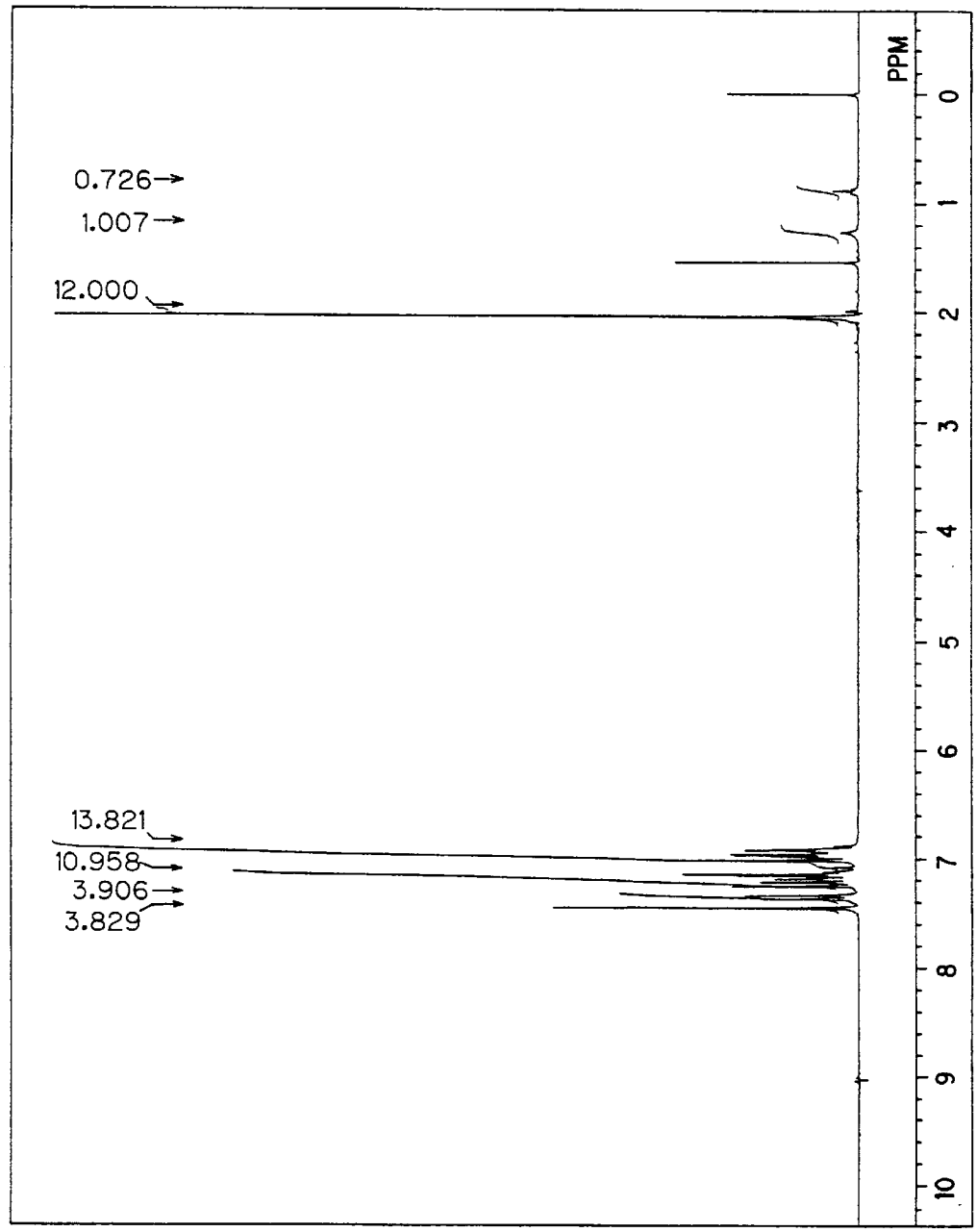
FIG. 1 is a graph illustrating a $^1$H-NMR spectrum of a stilbene derivative (11-2) obtained in Synthesis Example 1.

Firstly, stilbene derivative (1) of the present invention will be described in detail hereinafter.

In the above general formula (1), examples of the alkyl group corresponding to $R^1$, $R^2$, $R^3$ and $R^4$ include those having 1 to 6 carbon atoms such as methyl, ethyl, n-propyl, isopropyl, n-butyl, isobutyl, s-butyl, t-butyl, pentyl, isopentyl, neopentyl, hexyl and the like, among which those having 1 to 4 carbon atoms such as methyl, ethyl, n-propyl, isopropyl, n-butyl, isobutyl, s-butyl, t-butyl and the like are particularly preferred.

Further, the alkyl group corresponding to $R^1$, $R^2$, $R^3$ and $R^4$ optionally have a substituent such as hydroxyalkyl group, alkoxyalkyl group, alkylaminoalkyl group, dialkylaminoalkyl group, halogenated alkyl group, alkoxycarbonylalkyl group, carboxyalkyl group, alkanoyloxyalkyl group, aminoalkyl group and the like.

Especially, in the stilbene derivative (1) of the present invention, the alkyl groups which have substituents of electron donating groups such as alkoxy group, alkylamino group, dialkylamino group, amino group and the like are preferred in view of improving the hole transferring capability.

Examples of the hydroxyalkyl group include those having 1 to 6 carbon atoms in the alkyl moiety such as hydroxymethyl, 2-hydroxyethyl, 1,1-dimethyl-2-hydroxyethyl, 3-hydroxypropyl, 4-hydroxybutyl, 2-hydroxybutyl, 1-hydroxypentyl, 6-hydroxyhexyl and the like.

Examples of the alkoxyalkyl group include those having 1 to 6 carbon atoms in both the alkyl moiety and the alkoxy moiety such as methoxymethyl, methoxyethyl, methoxybutyl, ethoxyhexyl, ethoxymethyl, butoxyethyl, t-butoxyhexyl, hexyloxymethyl and the like.

Examples of the alkylaminoalkyl group include those having 1 to 6 carbon atoms in the alkyl moiety such as methylaminomethyl, ethylaminomethyl, hexylaminomethyl, ethylaminoethyl, hexylaminoethyl, methylaminopropyl, butylaminopropyl, methylaminobutyl, ethylaminobutyl, hexylaminobutyl, methylaminohexyl, ethylaminohexyl, butylaminohexyl, hexylaminohexyl and the like.

Examples of the dialkylaminoalkyl group include those having 1 to 6 carbon atoms in the alkyl moiety such as dimethylaminomethyl, diethylaminomethyl, dihexylaminomethyl, diethylaminoethyl, dihexylaminoethyl, dimethylaminopropyl, dibutylaminopropyl, dimethylaminobutyl, diethylaminobutyl, dihexylaminobutyl, dimethylaminohexyl, diethylaminohexyl, dibutylaminohexyl, dihexylaminohexyl and the like.

Examples of the alkoxycarbonylalkyl group include those having 1 to 6 carbon atoms in both the alkyl moiety and alkoxy moiety such as methoxycarbonylmethyl, methoxycarbonylethyl, methoxycarbonylhexyl, ethoxycarbonylmethyl, ethoxycarbonylethyl, propoxycarbonylmethyl, isopropoxycarbonylmethyl, buthoxycarbonylmethyl, pentyloxycarbonylmethyl, hexycarbonylmethyl, hexylcarbonylbutyl, hexylcarbylhexyl and the like.

Examples of carboxyalkyl group include those having 1 to 6 carbon atoms in the alkyl moiety such as carboxymethyl, carboxyethyl, carboxybutyl, carboxyhexyl, 1-methyl-2-carboxyethyl and the like.

Examples of the halogenated alkyl group include alkyl groups having 1 to 6 carbon atoms which are substituted by 1 to 3 halogen atoms such as monochlormethyl, monobromomethyl, monoiodomethyl, monofluoromethyl, dichlormethyl, dibromomethyl, diiodomethyl, difluoromethyl, trichlormehyl, tribromomethyl, triiodomethyl, trifluoromethyl, monochlorethyl, monobromoethyl, monoiodoethyl, monofluoroethyl, dibromobutyl, diiodobutyl, difluorobutyl, chlorhexyl, bromohexyl, iodohexyl, fluorohexyl.

Examples of alkanoyloxyalkyl group include alkanoyloxy groups having 2 to 6 carbon atoms in the alkanoyl moiety and 1 to 6 carbon atoms in the alkyl moiety such as acetoxymethyl, 2-acetoxyethyl, propionyloxymethyl, 1-hexanoyloxy-2-methylpentyl and the like.

Examples of aminoalkyl group include aminoalkyl groups having 1 to 6 carbon atoms in the alkyl moiety such as aminomethyl, aminoethyl, aminopropyl, aminobutyl, aminohexyl and the like.

Examples of alkoxy group corresponding to $R^1$, $R^2$, $R^3$ and $R^4$ include those having 1 to 6 carbon atoms such as methoxy, ethoxy, propoxy, isopropoxy, butoxy, t-butoxyl, pentyloxyl, hexyloxy and the like. Further, these alkoxy groups are optionally substituted by halogen atom, amino group, hydroxyl group, carboxyl group, alkanoyloxy group and the like, as mentioned above as a substituent for alkyl group.

Examples of aryl group corresponding to $R^1$ and $R^3$ include groups such as phenyl, naphtyl, anthoryl, phenanthoryl and the like.

Examples of aralkyl group corresponding to $R^1$ and $R^3$ include those having 1 to 6 carbon atoms in the alkyl moiety such as benzyl1-phenylethyl, 3-phenylpropyl, 4-phenylbutyl, 5-phenylpentyl, 6-phenylhexyl and the like.

The aryl group and aralkyl group optionally have substituents, examples of which include halogen atom, amino group, hydroxyl group, carboxyl group which are optionally esterified, ciano group and the like in addition to the above-mentioned alkyl groups having 1 to 6 carbon atoms and alkoxy groups having 1 to 6 carbon atoms. Further, substitution positions of these substituents are not necessarily specified.

The stilbene derivative (1) of the present invention includes the following general formulas (11) to (13) according to a difference in substitution position on a center benzene ring. Among them, a stilbene derivative represented by the general formula (11) or (12) is particularly preferred.

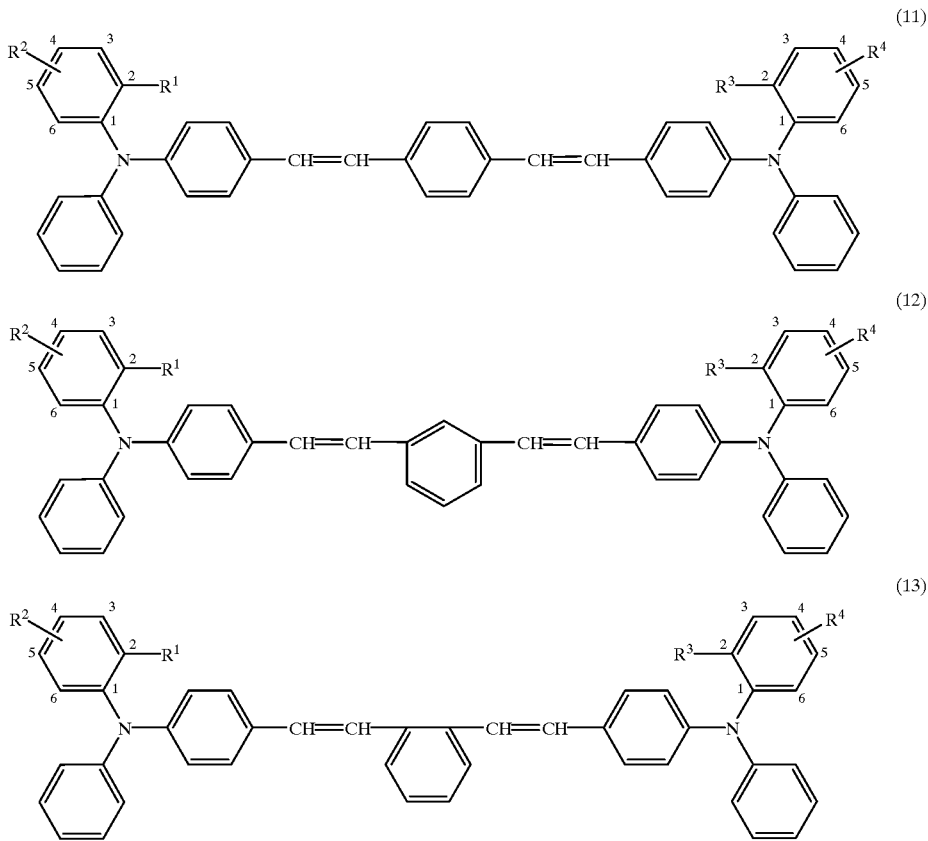

(wherein $R^1$ to $R^4$ are as defined above).

As the specific examples of the stilbene derivative represented by the above general formula (1), substituents corresponding to $R^1$ to $R^4$ are shown in the following Tables 1 to 2. In Tables 1 to 2, those represented by a series of the compound numbers (11-1, 11-2, 11-3, . . . ) are stilbene derivatives included in the general formula (11) whereas those represented by a series of the compound numbers (12-1, 12-2, 12-3, . . . ) are stilbene derivatives included in the general formula (12).

In Tables 1 to 2, H represents a hydrogen atom, Me represents a methyl group, Et represents an ethyl group, i-Pr represents an isopropyl group, t-Bu represents a tert-butyl group, MeO represents a methoxy group, EtO represents an ethoxy group, Ph represents a phenyl group, and Bzl represents a benzyl group.

TABLE 1

| compound numbers | $R^1$ | $R^2$ | $R^3$ | $R^4$ |
|---|---|---|---|---|
| 11-1 | Me | H | Me | H |
| 11-2 | Me | 6-Me | Me | 6-Me |
| 11-3 | Me | 3-Me | Me | 3-Me |
| 11-4 | Me | 5-Me | Me | 5-Me |
| 11-5 | Et | H | Et | H |
| 11-6 | Et | 6-Me | Et | 6-Me |
| 11-7 | Et | 6-Et | Et | 6-Et |
| 11-8 | i-Pr | H | i-Pr | H |
| 11-9 | i-Pr | 6-Me | i-Pr | 6-Me |
| 11-10 | t-Bu | H | t-Bu | H |
| 11-11 | t-Bu | 5-t-Bu | t-Bu | 5-t-bu |

TABLE 1-continued

| compound numbers | $R^1$ | $R^2$ | $R^3$ | $R^4$ |
|---|---|---|---|---|
| 11-12 | Ph | H | Ph | H |
| 11-13 | Bzl | H | Bzl | H |
| 11-14 | MeO | H | MeO | H |
| 11-15 | EtO | H | EtO | H |
| 11-16 | MeO | Me | MeO | Me |

TABLE 2

| compound numbers | $R^1$ | $R^2$ | $R^3$ | $R^4$ |
|---|---|---|---|---|
| 12-1 | Me | H | Me | H |
| 12-2 | Me | 6-Me | Me | 6-Me |
| 12-3 | Me | 3-Me | Me | 3-Me |
| 12-4 | Me | 5-Me | Me | 5-Me |
| 12-5 | Et | H | Et | H |
| 12-6 | Et | 6-Me | Et | 6-Me |
| 12-7 | Et | 6-Et | Et | 6-Et |
| 12-8 | i-Pr | H | i-Pr | H |
| 12-9 | i-Pr | 6-Me | i-Pr | 6-Me |
| 12-10 | t-Bu | H | t-Bu | H |
| 12-11 | t-Bu | 5-t-Bu | t-Bu | 5-t-bu |
| 12-12 | Ph | H | Ph | H |
| 12-13 | Bzl | H | Bzl | H |
| 12-14 | MeO | H | MeO | H |
| 12-15 | EtO | H | EtO | H |
| 12-16 | MeO | 6-Me | MeO | 6-Me |

TABLE 2-continued

| compound numbers | $R^1$ | $R^2$ | $R^3$ | $R^4$ |
|---|---|---|---|---|
| 12-17 | MeO | 5-Me | Meo | 5-Me |
| 12-18 | Me | 5-Meo | Me | 5-MeO |

The method of synthesizing the stilbene derivative (1) of the present invention will be described by way of the case where $R^1$ and $R^3$ are the same groups and $R^2$ and $R^4$ are the same groups as the example.

Reaction scheme (I):

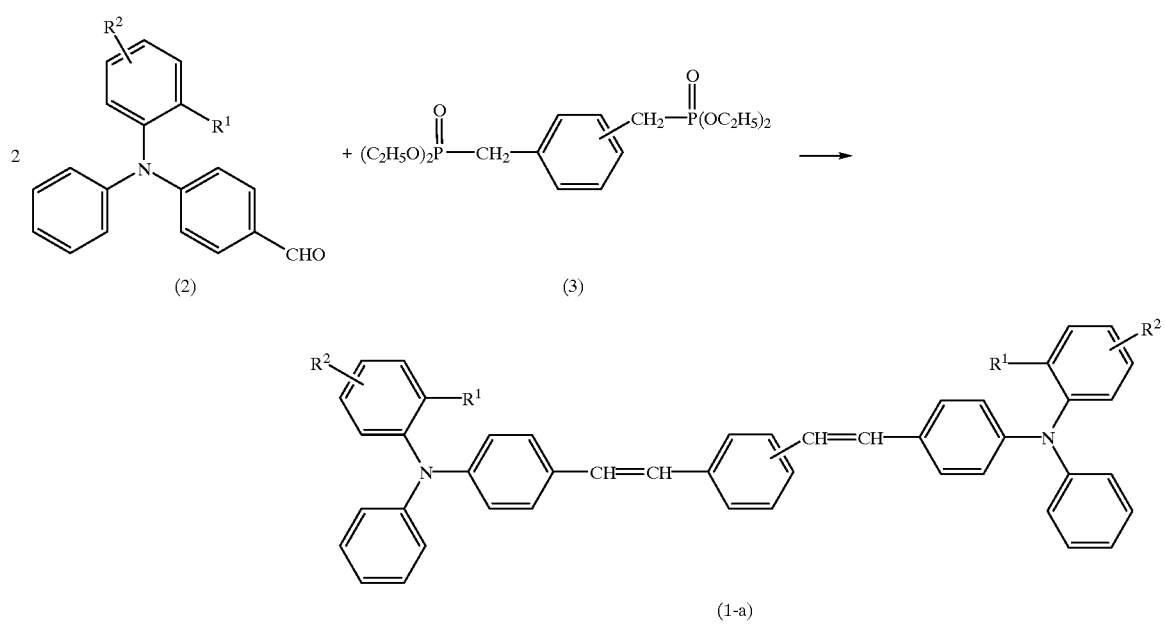

(wherein $R^1$ and $R^2$ are as defined above).

According to this reaction, a stilbene derivative represented by the general formula (1-a) of the present invention is obtained by reacting a formyl compound of triphenylamine, which is represented by the general formula (2), with a bisphosphate derivative (3) in a suitable anhydrous solvent in the presence of a base.

The solvent used in the above reaction may be any one which does not exert an influence on the reaction, and examples thereof include ethers such as diethyl ether, tetrahydrofuran, dioxane and the like; halogenated hydrocarbons such as methylene chloride, chloroform, dichloroethane and the like; and aromatic hydrocarbons such as benzene, toluene and the like.

Examples of the above base include sodium alkoxide such as sodium methoxide and metal hydride such as sodium hydride.

The amount of the base is at least from 2 to 4 times, and preferably from 2 to 2.5 times in a molar ratio, per mol of the bisphosphate derivative (3).

The amount of the compound (2) is from 1.8 to 2.5 times, and preferably from 1.95 to 2.05 times in a molar ratio, per mol of the bisphosphate derivative (3). The reaction is normally performed at −10 to 25° C., and is completed within the range from about 3 to 12 hours.

Reaction scheme (II):

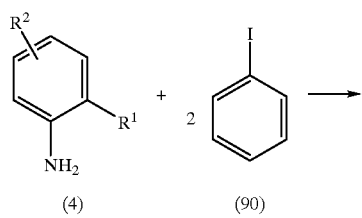

-continued

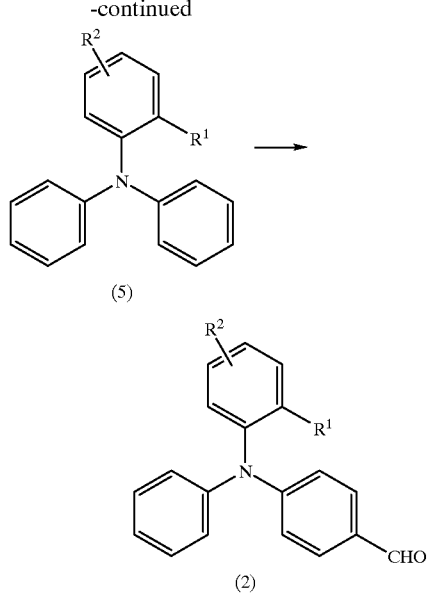

(wherein $R^1$ and $R^2$ are as defined above).

According to this reaction, a formyl compound (2) of triphenylamine as a starting material of the above reaction scheme (1-a) is obtained by adding an aniline derivative (4) and iodobenzene (90) in nitrobenzene to cause a reaction between them together with a catalyst such as anhydrous potassium carbonate, copper or the like to obtain a triphenylamine derivative (5) and then formylating this triphenylamine derivative (5) by the Vilsmeier method.

The ratio of the above aniline derivative (4) to iodobenzene (90) to be used is from 1:1.7 to 1:3, and preferably from 1:1.8 to 1:2.2, in a molar ratio. The reaction is normally performed at 160 to 220° C., and is completed within the range from about 4 to 30 hours.

A reagent (Vilsmeier reagent) used in the above Vilsmeier method is prepared by a combination of (i) a halogenating agent such as phosphorous oxychloride, phosgene, oxalyl chloride, thionyl chloride, triphenylphosphine-bromine, hexachlorotriphosphazatriene or the like with (ii) N,N-dimethylformamide (DMF), N-methylformanilide (MFA), N-formylmorpholine, N,N-diisopropylformamide or the like. In the present invention, a combination of phosphorous oxychloride with DMF which can also be used as the solvent, is employed particularly preferably.

In the preparation of the above Vilsmeier reagent, the ratio of the above (i) to (ii) to be used is normally from 1:1 to 1:2, and preferably from 1:1 to 1:1.2.

The amount of the above Vilsmeier reagent is from 0.9 to 2 times, and preferably from 1 to 1.1 times in a molar ratio, per mol of the triphenylamine derivative (5). The formylation of the above compound (5) is normally performed at 40 to 80° C. and is completed within the range from about 2 to 5 hours.

In the stilbene derivative (1) according to the present invention, the stilbene derivative having a substituted alkyl group for $R^1$ and/or $R^2$, for example $R^1$ is a hydroxy alkyl group, may be synthesized by (1) a method of using an aniline derivative having a hydroxy alkyl group as a starting compound or (2) a method wherein the stilbene derivative having an alkyl group for $R^1$ is synthesized and then said alkyl group is converted to a hydroxalkyl group by conventional means, for example, oxidation.

Reaction scheme (III):

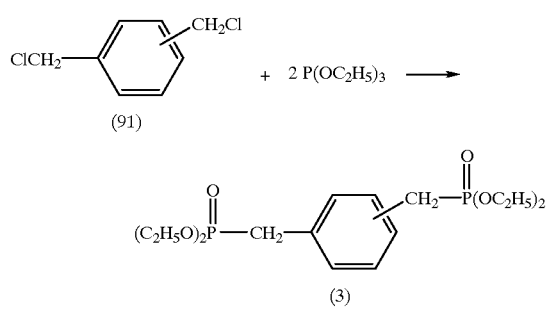

According to this reaction, a bisphosphate derivative (3) as a starting material of the above reaction scheme (1-a) is obtained by reacting α,α'-dichloroxylene (91) with a phosphorous acid or in a soithout using a solvent or in a solvent. The reaction is promoted when tertiary amine is added to remove a halogenated alkyl from the reaction system.

The solvent used in the above reaction may be any one which does not exert an influence on the reaction, and examples thereof include ethers such as diethyl ether, tetrahydrofuran, dioxane and the like; halogenated hydrocarbons such as methylene chloride, chloroform, dichloroethane and the like; aromatic hydrocarbons such as benzene, toluene and the like; and dimethylformamide.

Examples of the above tertiary amine include triethylamine, tributylamine, pyridine, 4-(dimethylamino) pyridine and the like.

The amount of the phosphorous acid triester is at least 2 times, and preferably from 2 to 2.4 times in a molar ratio, per mol of α, α'-dichloroxylene (91). The reaction is normally performed at 80 to 150° C. and is completed within the range from about 1 to 4 hours.

Among the stilbene derivative (1), a compound wherein $R^1$ and $R^3$ or $R^2$ and $R^4$ are different groups is synthesized by reacting a monophosphate derivative in place of the above bisphosphate derivative (3) with formyl compounds (2) and (2') of triphenylamine, which have different groups, in order.

Specifically, as shown in the following scheme (IV), methylbenzyl chloride (92) is first reacted with a phosphorous acid triester to obtain a monophosphate (93). Then, this monophosphate (93) is reacted with the above formyl compound (2) of triphenylamine to obtain a monostilbene derivative (94), which is chlorinated to obtain a compound (95).

Reaction scheme (IV):

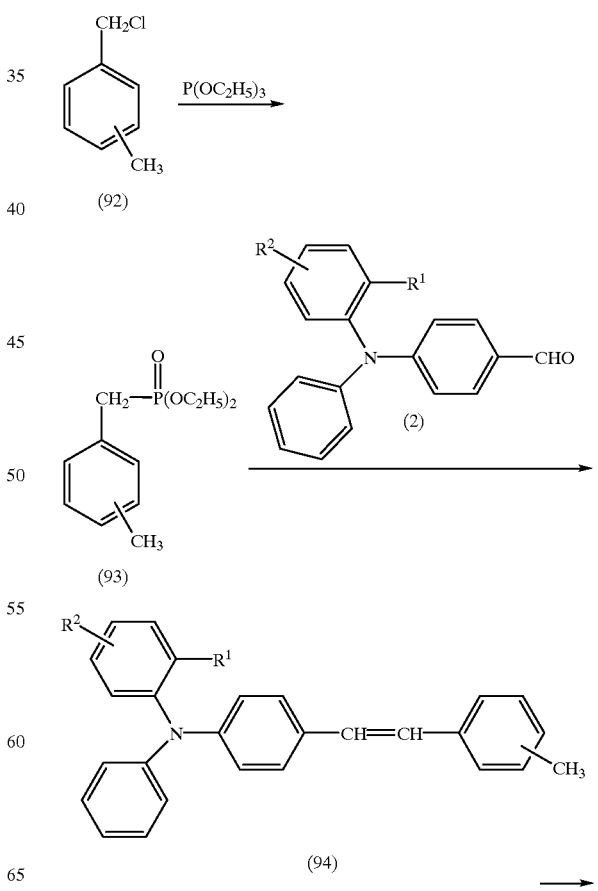

-continued

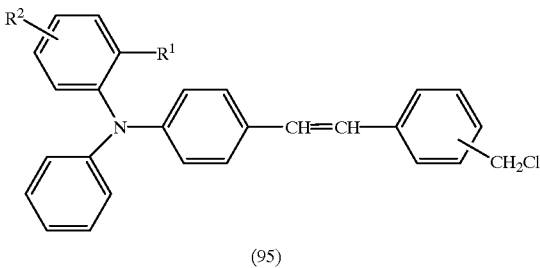

(95)

(wherein R¹ and R² are as defined above).

Then, as shown in the following reaction scheme (V), a stilbene derivative (1-b) is obtained by reacting the above compound (95) with a phosphorous acid triester to obtain a compound (96) and reacting the compound with a formyl compound (2') of triphenylamine.

Reaction scheme (V):

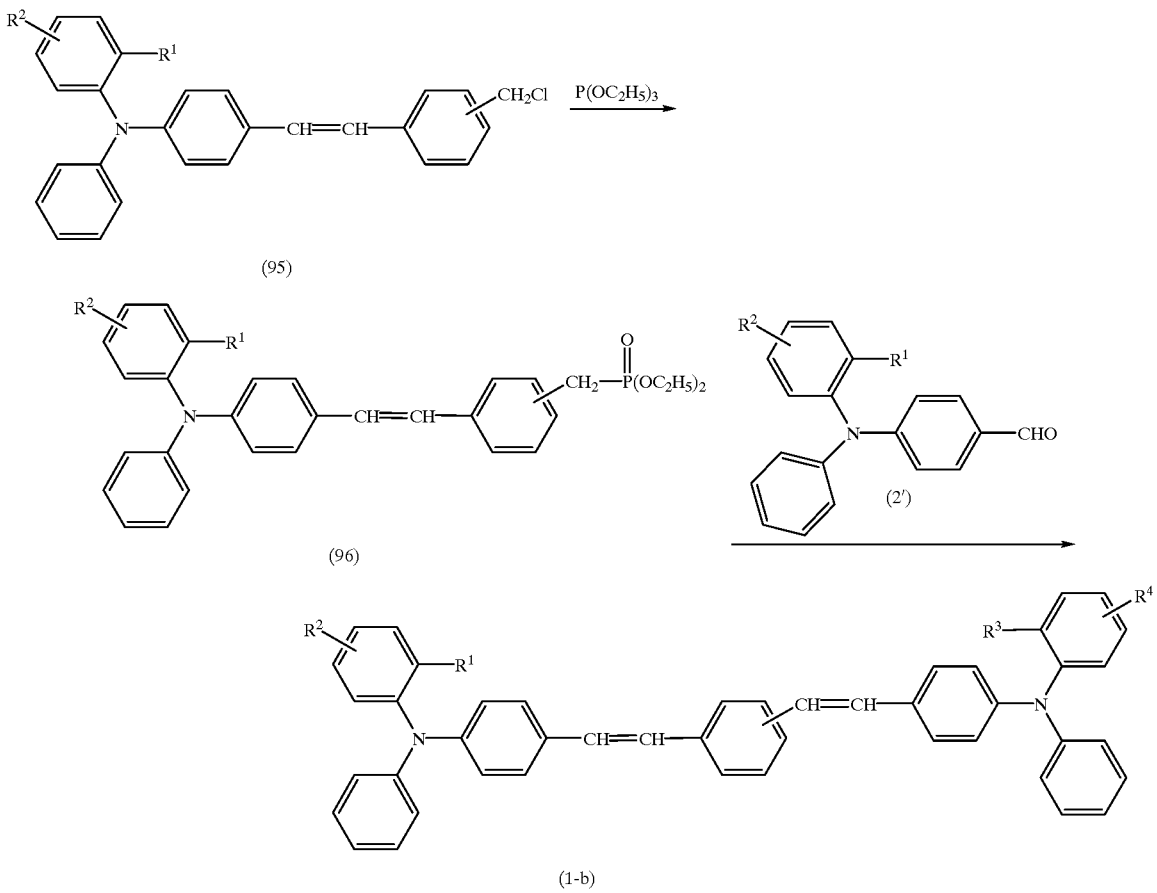

(wherein R¹ to R⁴ are as defined above).

The stilbene derivative represented by the above general formula (1) can be suitably used as a hole transferring material in the electrophotosensitive material and can also be used in various fields such as solar battery, electroluminescence device and the like because of large electric charge mobility, that is, because of high hole transferring capability as described above.

The electrophotosensitive material of the present invention will be described hereinafter.

The electrophotosensitive material of the present invention is obtained by providing a photosensitive layer containing the stilbene derivative represented by the above general formula (1) on a conductive substrate. The electrophotosensitive material may be a single-layer type or a multi-layer type as described above, but the present invention can be applied to both of them.

The single-layer type electrophotosensitive material is that obtained by providing a single photosensitive layer on a conductive substrate. This photosensitive layer is formed by dissolving or dispersing a stilbene derivative (hole transferring material) represented by the general formula (1), an electric charge generating material, a binding resin and, if necessary, an electron transferring material in a suitable solvent, applying the resulting coating solution on a conductive substrate and drying the coating solution. Such a single-layer type photosensitive material can be applied to both positive charging and negative charging type in a single construction, and the productivity is excellent because of simple layer construction.

Regarding the single-layer type electrophotosensitive material of the present invention, the residual potential of the photosensitive material is considerably lowered and the sensitivity is improved in comparison with a conventional single-layer type electrophotosensitive material.

On the other hand, the multi-layer type electrophotosensitive material is obtained by first providing an electric charge generating layer containing an electric charge generating material on a conductive substrate using a means such as vapor deposition, application or the like, applying a coating solution containing at least one stilbene derivative (hole transferring material) represented by the general formula (1) and a binding resin on this electric charge generating layer, and drying the coating solution to form an electric charge transferring layer. To the contrary, the electric charge transferring layer may be formed on the conductive substrate and the electric charge generating layer may be formed thereon. Since the electric charge generating layer has a considerably small film thickness in comparison with the electric charge transferring layer, it is preferred that the electric charge generating layer is formed on the conductive substrate and the electric charge transferring layer is formed thereon in order to protect the electric charge generating layer.

The charging type (positive or negative) of the electrophotosensitive material is selected according to the order of formation of the above electric charge generating layer and electric charge transferring layer and the kind of the electric charge transferring material used in the electric charge transferring layer. For example, in a case where the electric charge generating layer is formed on the conductive substrate and the electric charge transferring layer is formed thereon, as described above and the hole transferring material such as stilbene derivative (1) of the present invention is used as the electric charge transferring material in the electric charge transferring layer, the resulting photosensitive material becomes a negative charging type.

Regarding the multi-layer type electrophotosensitive material of the present invention, the residual potential of the photosensitive material is considerably lowered and the sensitivity is improved in comparison with the multi-layer type electrophotosensitive material using a conventional stilbene derivative as the hole transferring material.

As described above, the electrophotosensitive material of the present invention can be applied to both of the single-layer type and multi-layer type. The single-layer type is preferred because of the following reason. That is, the single-layer type can be used in both (negative and positive) charging types and can be easily produced because of its simple structure. Furthermore, film failures can be inhibited at the time of formation of the film and the optical characteristics can be improved because of small interlaminar surface.

Materials to be used in the present elelctrophotosensitive are hereinafter explained.

<Electric Charge Generating Material>

Examples of the electric charge generating material used in the present invention include compounds represented by the following general formulas (CG1) to (CG12).

(CG1) Metal-free phthalocyanine

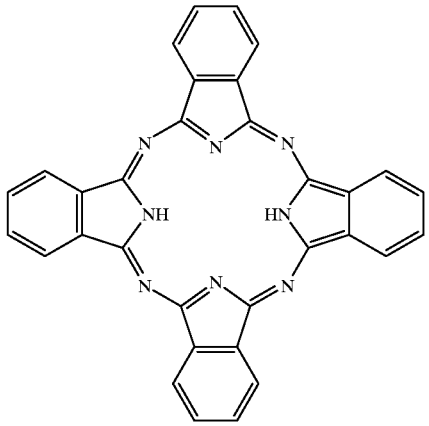

(CG2) Oxotitanyl phthalocyanine

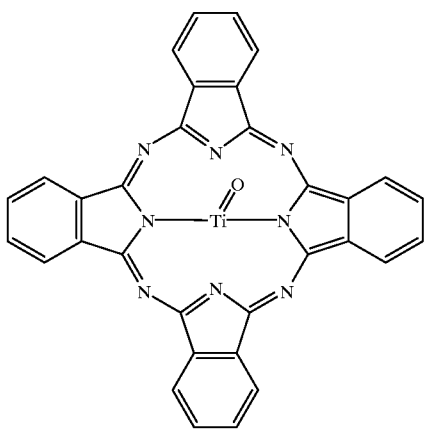

(CG3) Perylene pigment

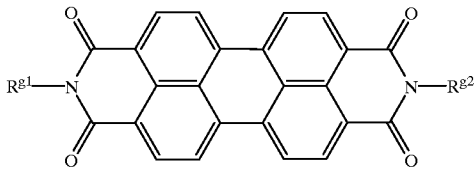

(wherein $R^{g1}$ and $R^{g2}$ are the same or different and represent a substituted or non-substituted alkyl group having 18 or less carbon atoms, a cycloalkyl group, an aryl group, an alkanoyl group or an aralkyl group)

(CG4) Bisazo pigment $$Cp^1-N=N-Q-N=N-Cp^2 \quad (CG4)$$

[wherein $Cp^1$ and $Cp^2$ are the same or different and represent a coupler residue; and Q represents groups represented by the following formulas:

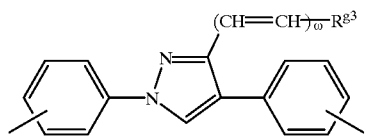
(Q-1)

(wherein $R^{g3}$ represents a hydrogen atom, an alkyl group, an aryl group or a heterocyclic group, and the alkyl group, aryl group or heterocyclic group may have a substituent; and ω represents 0 or 1),

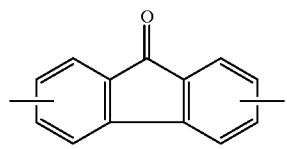
(Q-2)

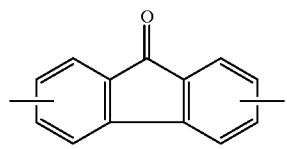
(Q-3)

(wherein $R^{g4}$ and $R^{g5}$ are the same or different and represents a hydrogen atom, an alkyl group having 1 to 5 carbon atoms, a halogen atom, an alkoxy group, an aryl group or an aralkyl group),

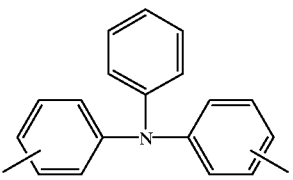
(Q-4)

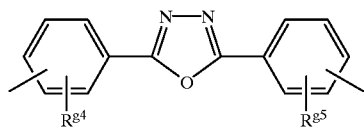
(Q-5)

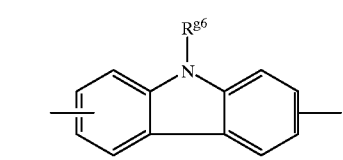
(Q-6)

(wherein $R^{g6}$ represents a hydrogen atom, an ethyl group, a chloroethyl group or a hydroxyethyl group),

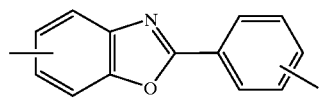
(Q-7)

or

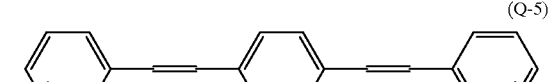
(Q-8)

(wherein $R^{g7}$, $R^{g8}$ and $R^{g9}$ are the same or different and represent a hydrogen atom, an alkyl group having 1 to 5 carbon atoms, a halogen atom, an alkoxy group, an aryl group or an aralkyl group)]

(CG5) Dithioketopyrrolopyrrole pigment

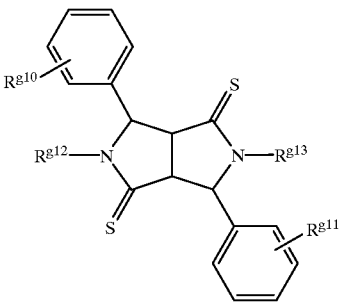
(CG5)

(wherein $R^{g10}$ and $R^{g11}$ are the same or different and represent a hydrogen atom, an alkyl group, an alkoxy group or a halogen atom; and $R^{g12}$ and $R^{g13}$ are the same or different and represent a hydrogen atom, an alkyl group or an aryl group)

(CG6) Metal-free naphthalocyanine pigment
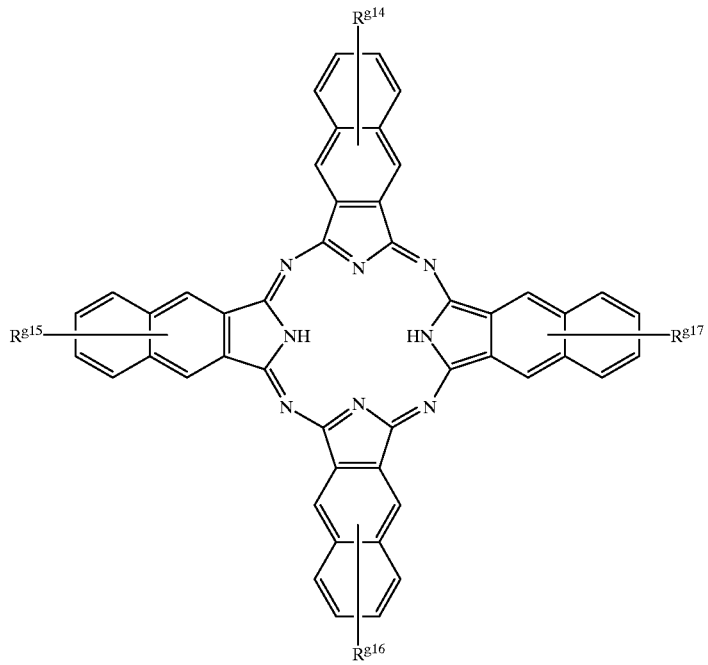
(wherein $R^{g14}$, $R^{g15}$, $R^{g16}$ and $R^{g17}$ are the same or different and represent a hydrogen atom, an alkoxy group or a halogen atom)
(CG7) Metal phthalocyanine pigment
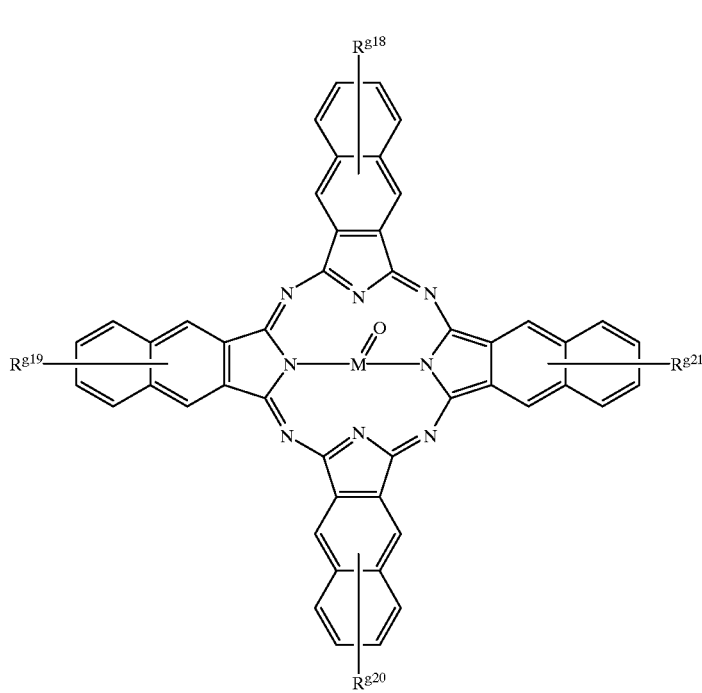
(wherein $R^{g18}$, $R^{g19}$, $R^{g20}$ and $R^{g21}$ are the same or different and represent a hydrogen atom, an alkyl group, an alkoxy group or a halogen atom; and M represents Ti or V)

(CG8) Squaline pigment

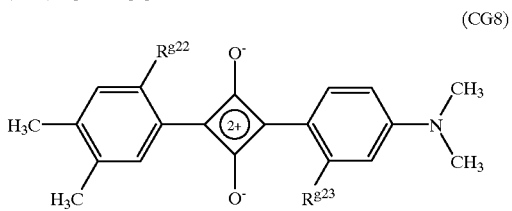
(CG8)

(wherein $R^{g22}$ and $R^{g23}$ are the same or different and represent a hydrogen atom, an alkyl group, an alkoxy group or a halogen atom)

(CG9) Trisazo pigment

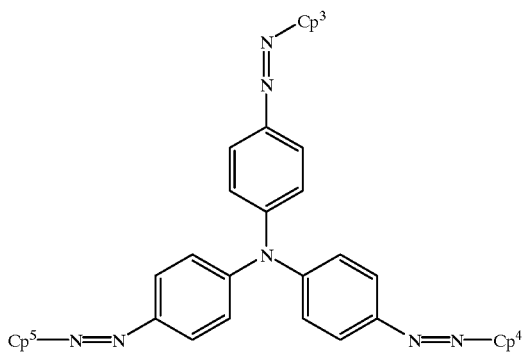
(CG9)

(wherein $Cp^3$, $Cp^4$ and $Cp^5$ are the same or different and represent a coupler residue)

(CG10) Indigo pigment

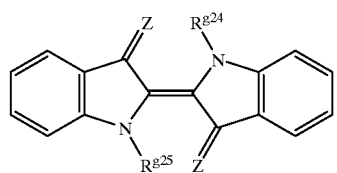
(CG10)

(wherein $R^{g24}$ and $R^{g25}$ are the same or different and represent a hydrogen atom, an alkyl group or an aryl group; and Z is an oxygen atom or a sulfur atom)

(CG11) Azulenium pigment

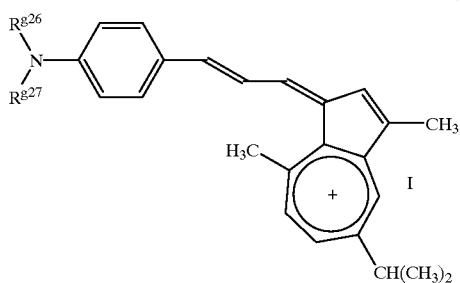
(CG11)

(wherein $R^{g26}$ and $R^{g27}$ are the same or different and represent a hydrogen atom, an alkyl group or an aryl group)

(CG12) Cyanine pigment

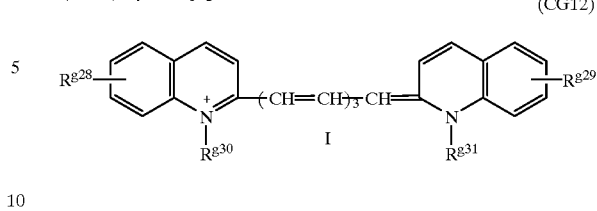
(CG12)

(wherein $R^{g28}$ and $R^{g29}$ are the same or different and represent a hydrogen atom, an alkyl group, an alkoxy group or a halogen atom; and $R^{g30}$ and $R^{g31}$ are the same or different and represent a hydrogen atom, an alkyl group or an aryl group)

In the above electric charge generating material, examples of the alkyl group include groups having 5 to 6 carbon atoms such as n-pentyl, n-hexyl and the like, in addition to the same groups as those described above. Examples of the substituted or non-substituted alkyl group having 18 or less carbon atoms include groups such as heptyl, octyl, nonyl, decyl, dodecyl, tridecyl, pentadecyl, octadecyl, etc., in addition to the alkyl groups having 1 to 6 carbon atoms.

Examples of the cycloalkyl group include groups having 3 to 8 carbon atoms such as cyclopropyl, cyclobutyl, cyclopentyl, cyclohexyl, cycloheptyl, cyclooctyl and the like.

Examples of the alkoxy group include groups having 1 to 6 carbon atoms such as methoxy, ethoxy, n-propoxy, isopropoxy, t-butoxy, n-pentyloxy, n-hexyloxy and the like.

Examples of the aryl group include groups such as phenyl, napthyl, anthryl, phenanthryl and the like. Examples of the alkanoyl group include formyl, acetyl, propionyl, butyryl, pentanoyl, hexanoyl and the like. Examples of the halogen atom include fluorine, chlorine, bromine, iodine and the like.

Examples of the heterocyclic group include thienyl, furyl, pyrrolyl, pyrrolidinyl, oxazolyl, isoxazolyl, thiazolyl, isothiazolyl, imidazolyl, 2H-imidazoyl, pyrazolyl, triazolyl, tetrazolyl, pyranyl, pyridyl, piperidyl, piperidino, 3-morpholinyl, morpholino, thiazolyl and the like. The heterocyclic group may also be ones condensed with an aromatic ring.

Examples of the substituent which may be substituted on the above groups include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group and the like.

Examples of the coupler residue represented by $Cp^1$, $Cp^2$, $Cp^3$, $Cp^4$ and $Cp^5$ include the groups shown in the following general formulas (Cp-1) to (Cp-11).

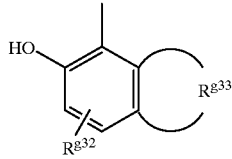
(Cp-1)

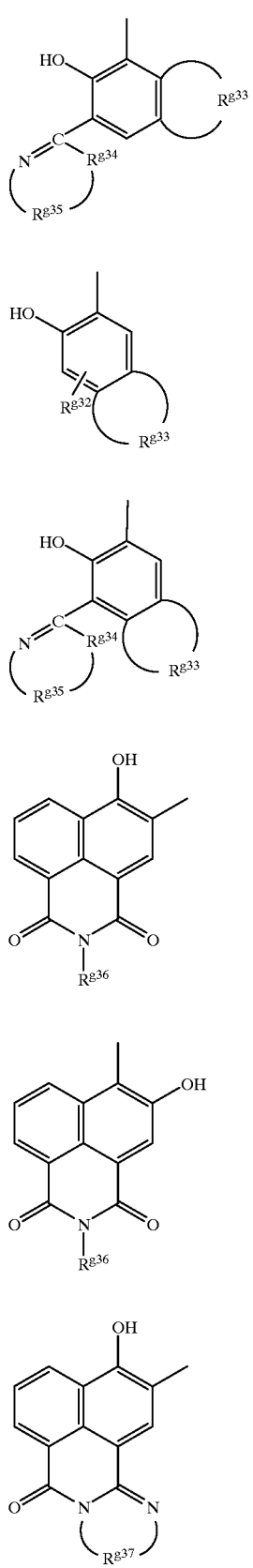

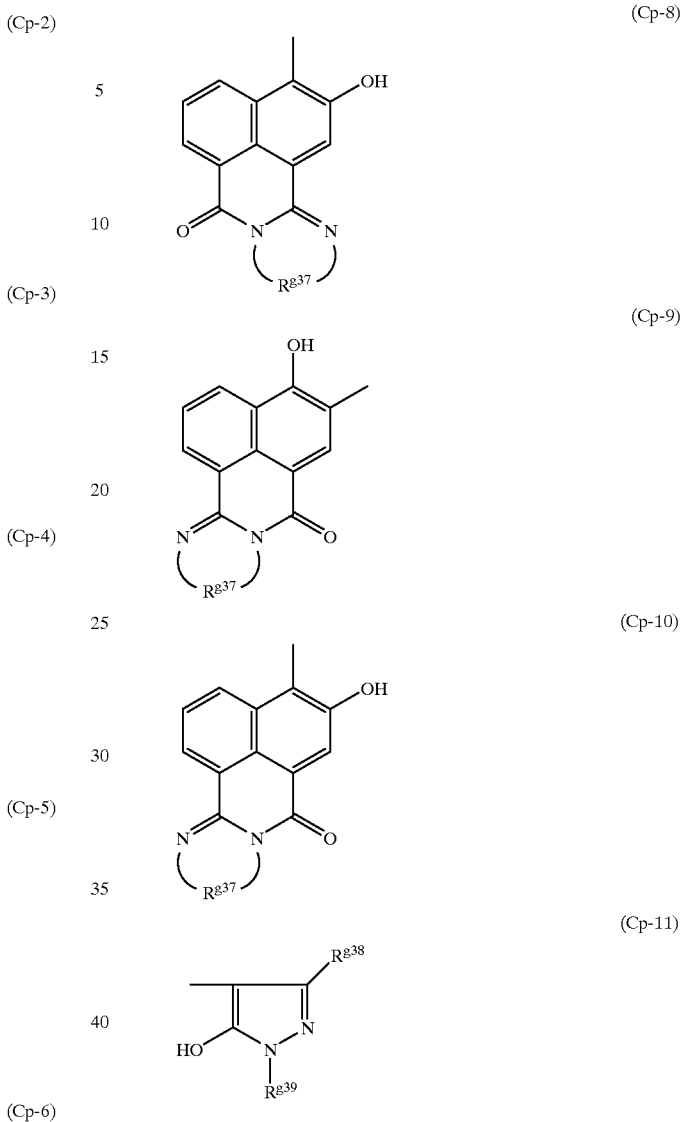

In the respective formulas, $R^{g32}$ is a carbamoyl group, a sulfamoyl group, an allophanoyl group, oxamoyl group, anthraniloyl group, carbazoyl group, glycyl group, hydantoyl group, phthalamoyl group or a succinamoyl group. These groups may have substituents such as halogen atom, phenyl group which may have a substituent, naphthyl group which may have a substituent, nitro group, cyano group, alkyl group, alkenyl group, carbonyl group, carboxyl group and the like.

$R^{g33}$ is an atomic group which is required to form an aromatic ring, a polycyclic hydrocarbon or a heterocycle by condensing with a benzene ring. These rings may have the same substituent as that described above.

$R^{g34}$ is an oxygen atom, a sulfur atom or an imino group.

$R^{g35}$ is a divalent chain hydrocarbon or an aromatic hydrocarbon group, and these groups may have the same substituent as that described above.

$R^{g36}$ is an alkyl group, an aralkyl group, an aryl group or a heterocyclic group. These groups may have the same substituent as that described above.

$R^{g37}$ is an atomic group which is required to form a heterocycle together with a divalent chain hydrocarbon or aromatic hydrocarbon group or two nitrogen atoms in the above formulas (Cp-1) to (Cp-2). These rings may have the same substituent as that described above.

$R^{g38}$ is a hydrogen atom, an alkyl group, an amino group, a carbamoyl group, a sulfamoyl group, an allophanoyl group, a carboxyl group, an alkoxycarbonyl group, an aryl group or a cyano group. The groups other than a hydrogen atom may have the same substituent as that described above.

$R^{g39}$ is an alkyl group or an aryl group which may have the same substituent as that described above.

Examples of the alkenyl group include alkenyl groups having 2 to 6 carbon atoms such as vinyl, allyl, 2-butenyl, 3-butenyl, 1-methylallyl, 2-pentenyl, 2-hexenyl and the like.

In the above $R^{g33}$, examples of the atomic group which is required to form an aromatic ring by condensing with a benzene ring include alkylene groups having 1 to 4 carbon atoms such as methylene, ethylene, trimethylene, tetramethylene and the like.

Examples of the aromatic ring to be formed by condensing the above $R^{g33}$ with a benzene ring include naphthalene ring, anthracene ring, phenanthrene ring, pyrene ring, chrysene ring, naphthacene ring and the like.

In the above $R^{g33}$, examples of the atomic group which is required to form a polycyclic hydrocarbon by condensing with a benzene ring include the above alkylene groups having 1 to 4 carbon atoms, carbazole ring, benzocarbazole ring, dibenzofuran ring and the like.

In the above $R^{g33}$, examples of the atomic group which is required to form a heterocycle by condensing with a benzene ring include benzofuranyl, benzothiophenyl, indolyl, benzoxazolyl, 1H-indolyl, benzothiazolyl, lH-indadolyl, benzoimidazolyl, chromenyl, chromanyl, isochromanyl, quinolinyl, isoquinolinyl, cinnolinyl, phthalazinyl, quinazolinyl, quinoxalinyl, dibenzofranyl, carbazoyl, xanthenyl, acridinyl, phenanthridinyl, phenazinyl, phenoxazinyl, thianthrenyl and the like.

Examples of the aromatic heterocyclic group to be formed by condensing the above $R^{g33}$ and the benzene ring include thienyl, furyl, pyrrolyl, oxazolyl, isoxazolyl, thiazolyl, isothiazolyl, imidazolyl, pyrazolyl, triazolyl, tetrazolyl, pyridyl, thiazolyl and the like. In addition, it may also be a heterocyclic group condensed with other aromatic rings (e.g. benzofuranyl, benzoimidazolyl, benzoxazolyl, benzothiazolyl, quinolyl, etc.).

In the above $R^{g35}$ and $R^{g37}$, examples of the divalent chain hydrocarbon include ethylene, trimethylene, tetramethylene and the like. Examples of the divalent aromatic hydrocarbon include phenylene, naphthylene, phenanthrilene and the like.

In the above $R^{g36}$, examples of the heterocyclic group include pyridyl, pyrazyl, thienyl, pyranyl, indolyl and the like.

In the above $R^{g37}$, examples of the atomic group which is required to form a heterocycle together with two nitrogen atoms include phenylene, naphthylene, phenanthrylene, ethylene, trimethylene, tetramethylene and the like.

Examples of the aromatic heterocyclic group to be formed by the above $R^{g37}$ and two nitrogen atoms include benzoimidazole, benzo[f]benzoimidazole, dibenzo[e,g] benzoimidazole, benzopyrimidine and the like. These groups may have the same substituent as that described above.

In the above $R^{g38}$, examples of the alkoxycarbonyl group include groups such as methoxycarbonyl, ethoxycarbonyl, propoxycarbonyl, butoxycarbonyl and the like.

In the present invention, there can be used powders of inorganic photoconductive materials such as selenium, selenium-tellurium, selenium-arsenic, cadmium sulfide, amorphous silicon, etc. and known electric charge generating materials such as pyrilium salt, anthanthrone pigments, triphenylmethane pigments, threne pigments, toluidine pigments, pyrazoline pigments, quinacridone pigments, etc. in addition to the above electric charge generating materials.

The above electric charge generating materials can be used alone or in combination thereof to present an absorption wavelength within a desired range.

A photosensitive material having sensitivity at the wavelength range of 700 nm or more is required in digital-optical image forming apparatuses such as laser beam printer using a light source of semiconductor laser, facsimile and the like. Therefore, among the above electric charge generating materials, phthalocyanine pigments such as metal-free phthalocyanine represented by the above general formula (CG1), oxotitanyl phthalocyanine represented by the general formula (CG2) and the like are preferably used. The crystal form of the above phthalocyanine pigments is not specifically limited, and various phthalocyanine pigments having different crystal form can be used.

In analogue-optical image forming devices such as electrostatic copying machine using a white light source such as halogen lamp, etc., a photosensitive material having sensitivity at the visible range is required. Therefore, the perylene pigment represented by the above general formula (CG3) and bisazo pigment represented by the general formula (CG4) and the like are suitably used.

<Hole Transferring Material>

In the electrophotosensitive material of the present invention, a stilbene derivative (1) as the hole transferring material and other known hole transferring materials may be contained in the photosensitive layer.

Examples of the hole transferring material include various compounds having high hole transferring capability, for example, compounds represented by the following general formulas (HT1) to (HT13):

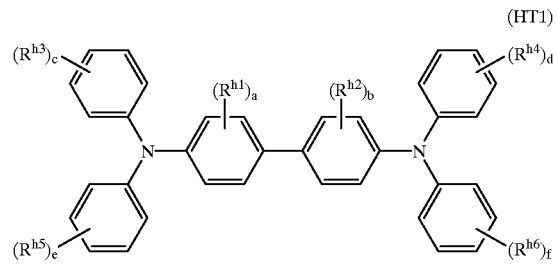
(HT1)

(wherein $R^{h1}$, $R^{h2}$, $R^{h3}$, $R^{h4}$, $R^{h5}$ and $R^{h6}$ are the same or different and represent a halogen atom, an alkyl group which may have a substituent, an alkoxy group which may have a substituent or an aryl group which may have a substituent; a and b are the same or different and represent an integer of 0 to 4; c, d, e and f are the same or different and represent an integer of 0 to 5; and each $R^{h1}$, $R^{h2}$, $R^{h3}$, $R^{h4}$, $R^{h5}$ and $R^{h6}$ may be different provided that a, b, c, d, e or f is 2 or more)

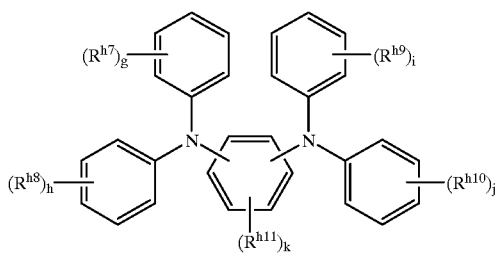
(HT2)

(wherein $R^{h7}$, $R^{h8}$, $R^{h9}$, $R^{h10}$ and $R^{h11}$ are the same or different and represent a halogen atom, an alkyl group which may have a substituent, an alkoxy group which may have a substituent or an aryl group which may have a substituent; g, h, i and j are the same or different and represent an integer of 0 to 5; k represents an integer of 0 to 4; and each $R^{h7}$, $R^{h8}$, $R^{h9}$, $R^{h10}$ and $R^{h11}$ may be different provided that g, h, i, j or k is 2 or more)

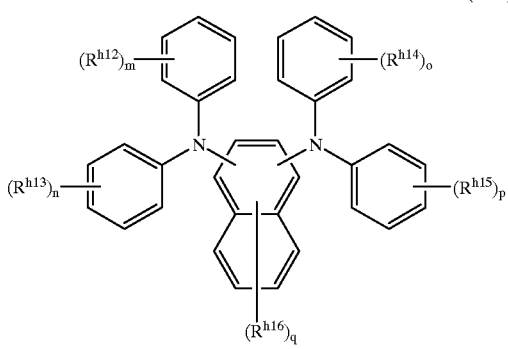
(HT3)

(wherein $R^{h12}$, $R^{h13}$, $R^{h14}$ and $R^{h15}$ are the same or different and represent a halogen atom, an alkyl group which may have a substituent, an alkoxy group which may have a substituent or an aryl group which may have a substituent; $R^{h16}$ is a halogen atom, a cyano group, a nitro group, an alkyl group which may have a substituent, an alkoxy which may have a substituent or an aryl group which may have a substituent; m, n, o and p are the same or different and represent an integer of 0 to 5; and q is an integer of 0 to 6; each $R^{h12}$, $R^{h13}$, $R^{h14}$, $R^{h15}$ and $R^{h16}$ may be different provided that m, n, o, p or q is 2 or more)

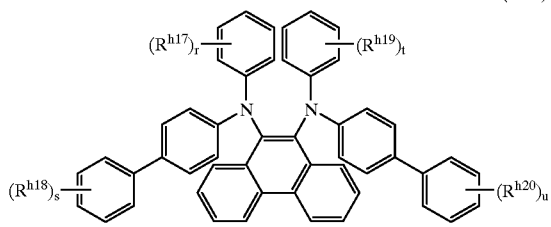
(HT4)

(wherein $R^{h17}$, $R^{h18}$, $R^{h19}$ and $R^{h20}$ are the same or different and represent a halogen atom, an alkyl group which may have a substituent, an alkoxy group which may have a substituent or an aryl group which may have a substituent; r, s, t and u are the same or different and represent an integer of 0 to 5; and that each $R^{h17}$, $R^{h18}$, $R^{h19}$ and $R^{h20}$ may be different provided that r, s, t or u is 2 or more)

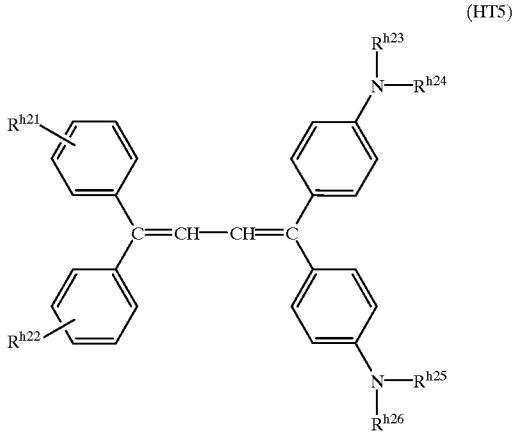
(HT5)

(wherein $R^{h21}$ and $R^{h22}$ are the same or different and represent a hydrogen atom, a halogen atom, an alkyl group or an alkoxy group, and $R^{h23}$, $R^{h24}$, $R^{h25}$ and $R^{h26}$ may be the same or different and represent a hydrogen atom, an alkyl group or an aryl group)

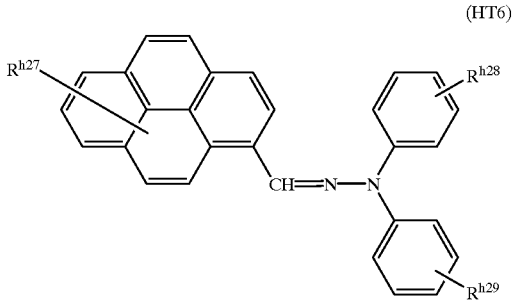
(HT6)

(wherein $R^{h27}$, $R^{h28}$ and $R^{h29}$ are the same or different and represent a hydrogen atom, a halogen atom, an alkyl group or an alkoxy group)

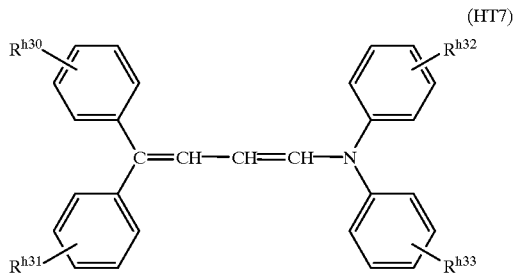
(HT7)

(wherein $R^{h30}$, $R^{h31}$, $R^{h32}$ and $R^{h33}$ may be the same or different and represent a hydrogen atom, a halogen atom, an alkyl group or an alkoxy group)

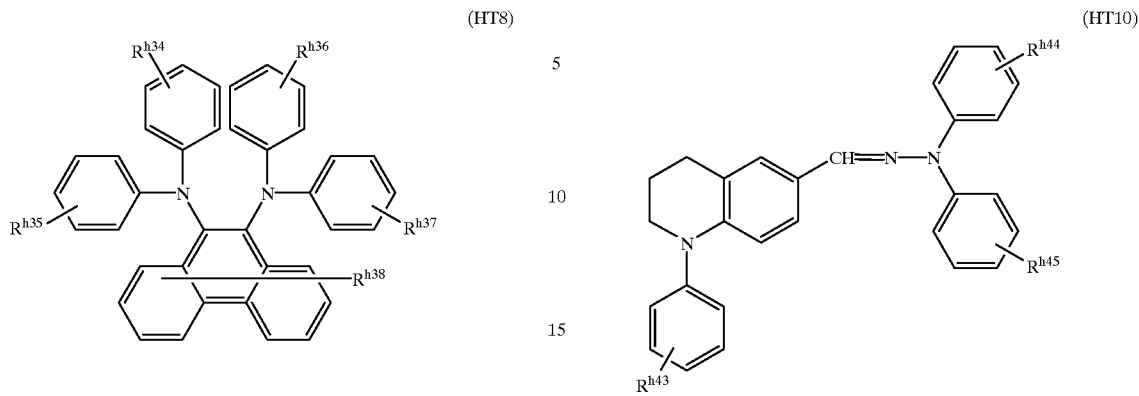

(wherein $R^{h34}$, $R^{h35}$, $R^{h36}$, $R^{h37}$ and $R^{h38}$ may be the same or different and represent a hydrogen atom, a halogen atom, an alkyl group or an alkoxy group)

(wherein $R^{h43}$, $R^{h44}$ and $R^{h45}$ may be the same or different and represent a hydrogen atom, a halogen atom, an alkyl group or an alkoxy group)

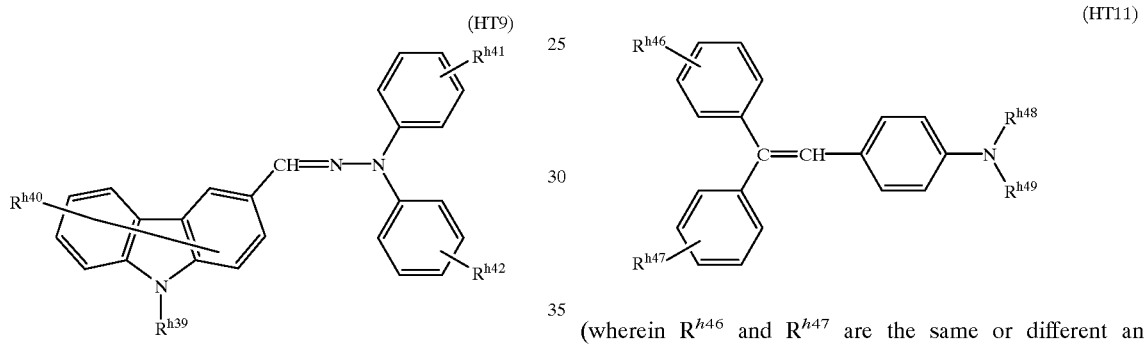

(wherein $R^{h39}$ is a hydrogen atom or an alkyl group, and $R^{h40}$, $R^{h41}$ and $R^{h42}$ may be the same or different and represent a hydrogen atom, a halogen atom, an alkyl group or an alkoxy group)

(wherein $R^{h46}$ and $R^{h47}$ are the same or different and represent a hydrogen atom, a halogen atom, an alkyl group which may have a substituent or an alkoxy group which may have a substituent; and $R^{h48}$ and $R^{h49}$ are the same or different and represent a hydrogen atom, an alkyl group which may have a substituent, or an aryl group which may have a substituent)

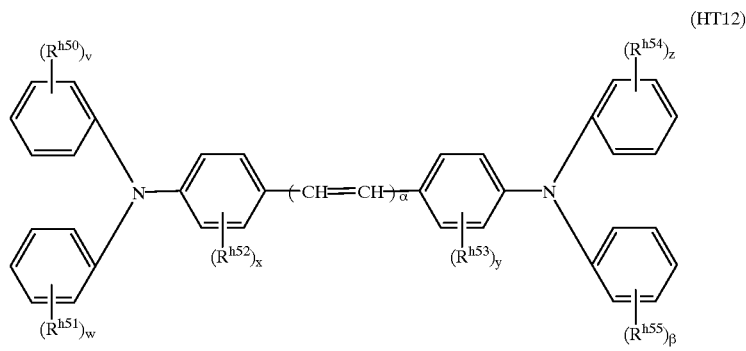

(wherein $R^{h50}$, $R^{h51}$, $R^{h52}$, $R^{h53}$, $R^{h54}$ and $R^{h55}$ are the same or different and represent an alkyl group which may have a substituent, an alkoxy group which may have a substituent or an aryl group which may have a substituent; α is an integer of 1 to 10; v, w, x, y, z and β are the same or different and represent an integer of 0 to 2; and each $R^{h50}$, $R^{h51}$, $R^{h52}$, $R^{h53}$, $R^{h54}$ and $R^{h55}$ may be different provided that v, w, x, y, z or β is 2)

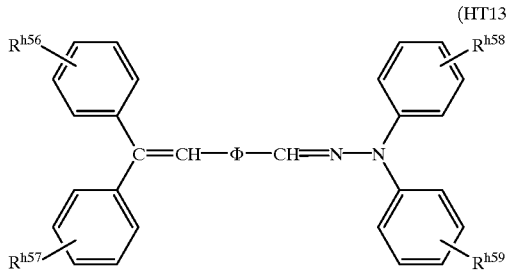

(HT13)

(wherein $R^{h56}$, $R^{h57}$, $R^{h58}$ and $R^{h59}$ may be the same or different and represent a hydrogen atom, a halogen atom, an alkyl group or an alkoxy group, and Φ represent a group represented by the formulas (Φ-1), (Φ-2) or (Φ-3):

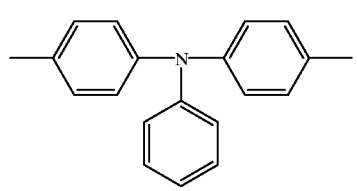

(Φ-1)

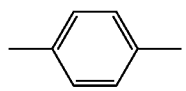

(Φ-2)

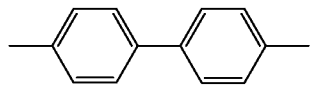

(Φ-3)

In the hole transferring material described above, examples of the alkyl group, alkoxy group, aryl group, aralkyl group and halogen atom include the same groups as those described above.

Examples of the substituent which may be substituted on the above groups include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc. The substitution position of the substituent is not specifically limited.

In the present invention, there can be used hole transferring materials which have hitherto been known, that is, nitrogen-containing cyclic compounds and condensed polycyclic compounds, e.g. oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organopolysilane compounds; pyrazoline compounds such as 1-phenyl-3-(p-dimethylaminophenyl)pyrazoline, etc.; hydrazone compounds; triphenylamine compounds; indole compounds; oxazole compounds; isoxazole compounds; thiazole compounds; thiadiazole compounds; imidazole compounds; pyrazole compounds; and triazole compounds, together with or in place of the above hole transferring materials (HT-1) to (HT-13).

In the present invention, these hole transferring materials may be used alone or in combination thereof. When using the hole transferring material having film forming properties, such as poly(vinylcarbazole), etc., a binding resin is not required necessarily.

<Electron Transferring Material>

Examples of the electron transferring materials include various compounds having high electron transferring capability, for example, compounds represented by the following general formulas (ET1) to (ET17):

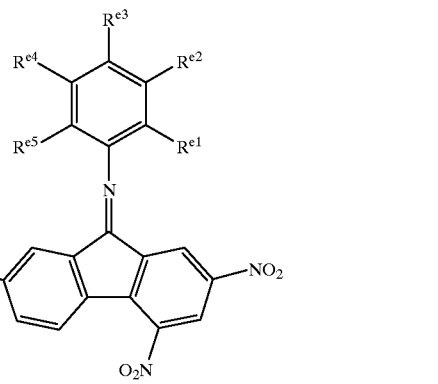

(ET1)

(wherein $R^{e1}$, $R^{e2}$, $R^{e3}$, $R^{e4}$ and $R^{e5}$ are the same or different and represent a hydrogen atom, an alkyl group which may have a substituent, an alkoxy group which may have a substituent, an aryl group which may have a substituent, an aralkyl group which may have a substituent, a phenoxy group which may have a substituent or a halogen atom)

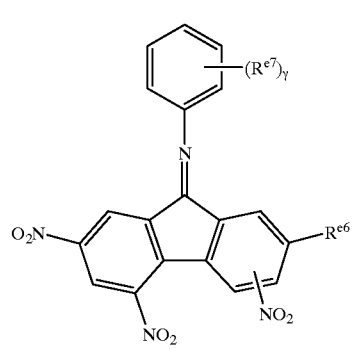

(ET2)

(wherein $R^{e6}$ represents an alkyl group; $R^{e7}$ represents an alkyl group which may have a substituent, an alkoxy group which may have a substituent, an aryl group which may have a substituent, an aralkyl group which may have a substituent, a halogen atom or a halogenated alkyl group; γ represents an integer of 0 to 5; and each $R^{e7}$ may be different provided that γ is 2 or more)

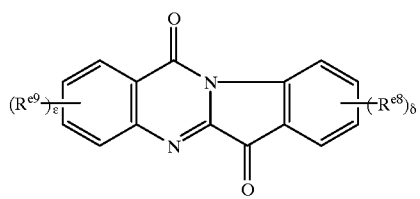
(ET3)

(wherein $R^{e8}$ and $R^{e9}$ may be the same or different and represent an alkyl group; δ represents an integer of 1 to 4; ε represents an integer of 0 to 4; and each $R^{e8}$ and $R^{e9}$ may be different provided that δ and ε are 2 or more)

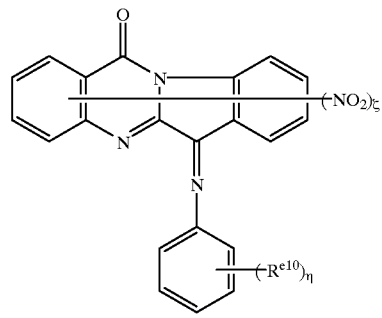
(ET4)

(wherein $R^{e10}$ represents an alkyl group, an aryl group, an aralkyl group, an alkoxy group, a halogenated alkyl group or a halogen atom; ζ represents an integer of 0 to 4; η represents an integer of 0 to 5; and each $R^{e10}$ may be different provided that η is 2 or more)

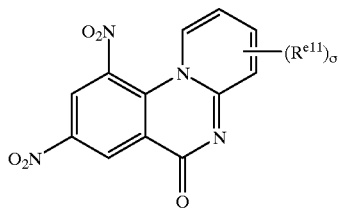
(ET5)

(wherein $R^{e11}$ represents an alkyl group; σ represents an integer of 1 to 4; and each Re11 may be different provided that σ is 2 or more)

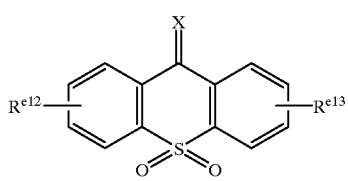
(ET6)

(wherein $R^{e12}$ and $R^{e13}$ are the same or different and represent a hydrogen atom, a halogen atom, an alkyl group, an aryl group, an aralkyloxycarbonyl group, an alkoxy group, a hydroxyl group, a nitro group or a cyano group; and X represents an oxygen atom, a =N—CN group or a =C(CN)$_2$ group)

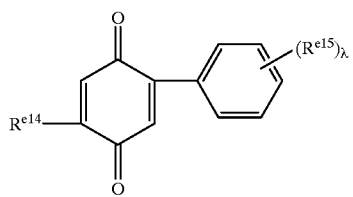
(ET7)

(wherein $R^{e14}$ represents a hydrogen atom, a halogen atom, an alkyl group or a phenyl group which may have a substituent; $R^{e15}$ represents a halogen atom, an alkyl group which may have a substituent, a phenyl group which may have a substituent, an alkoxycarbonyl group, a N-alkylcarbamoyl group, a cyano group or a nitro group; λ represents an integer of 0 to 3; and each $R^{e15}$ may be different provided that λ is 2 or more)

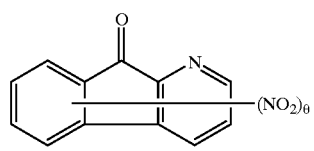
(ET8)

(wherein θ represents an integer of 1 to 2)

(ET9)

(wherein $R^{e16}$ and $R^{e17}$ are the same or different and represent a halogen atom, an alkyl group which may have a substituent, a cyano group, a nitro group or an alkoxycarbonyl group; and ν and ξ represent an integer of 0 to 3; and $R^{e16}$ and $R^{e17}$ may be different provided when ν or ξ is 2 or more)

(ET10)

$$R^{e18}-\underset{\underset{CN}{|}}{C}=CH-R^{e19}$$

(wherein $R^{e18}$ and $R^{e19}$ are the same or different and represent a phenyl group, a polycyclic aromatic group or a heterocyclic group, and these group may have a substituent)

(ET11)

(wherein $R^{e20}$ represents an amino group, a dialkylamino group, an alkoxy group, an alkyl group or a phenyl group; π represents an integer of 1 to 2; and each $R^{e20}$ may be different provided that π is 2)

(ET12)

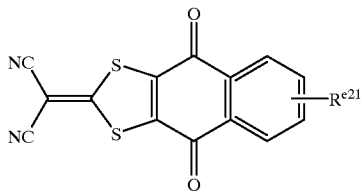

(wherein $R^{e21}$ represents a hydrogen atom, an alkyl group, an aryl group, an alkoxy group or an aralkyl group)

(ET13)

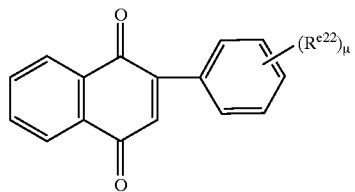

(wherein $R^{e22}$ represents a halogen atom, an alkyl group which may have a substituent, a phenyl group which may have a substituent, an alkoxycarbonyl group, a N-alkylcarbamoyl group, a cyano group or a nitro group; $\mu$ represents an integer of 0 to 3; and each $R^{e22}$ may be different provided that $\mu$ is 2 or more)

(ET14)

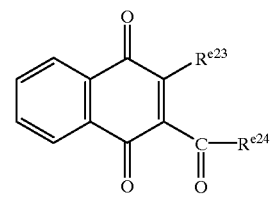

[(wherein $R^{e23}$ represents an alkyl group which may have a substituent or an aryl group which may have a substituent; and $R^{e24}$ represents an alkyl group which may have a substituent, an aryl which may have a substituent, or a group: —O—$R^{e24a}$ ($R^{e24a}$ represents an alkyl group which may have a substituent, or an aryl group which may have a substituent)]

(ET15)

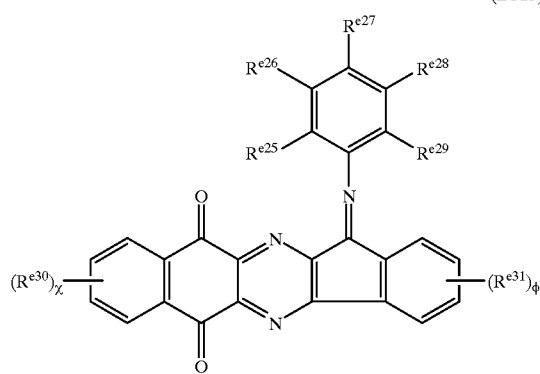

(wherein $R^{e25}$, $R^{e26}$, $R^{e27}$, $R^{e28}$, $R^{e29}$, $R^{e30}$ and $R^{e31}$ are the same or different and represent an alkyl group, aryl group, aralkyl group, alkoxy group, a halogen atom or a halogenated alkyl group; and $\chi$ and $\phi$ are the same or different and represent an integer of 0 to 4)

(ET16)

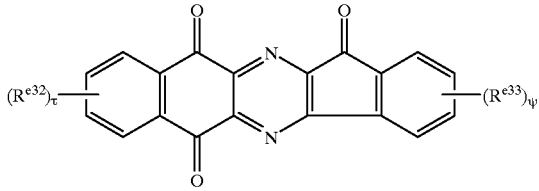

(wherein $R^{e32}$ and $R^{e33}$ are the same or different and represent an alkyl group, an aryl group, an alkoxy group, a halogen atom or a halogenated alkyl group; and $\tau$ and $\phi$ are the same or different and represent an integer of 0 to 4)

(ET17)

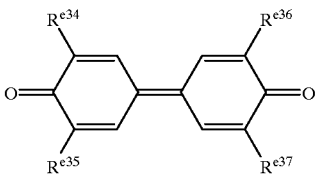

(wherein $R^{e34}$, $R^{e35}$, $R^{e36}$ and $R^{e37}$ are the same or different and represent a hydrogen atom, an alkyl group, alkoxy group, an aryl group, an aralkyl group, a cycloalkyl group or an amino group provided that at least two substituents of $R^{e34}$, $R^{e35}$, $R^{e36}$ and $R^{e37}$ are the same groups other than hydrogen atom).

In the above electron transferring materials, examples of the alkyl group, alkoxy group, aryl group, aralkyl group, cycloalkyl group, alkoxycarbonyl group, heterocyclic group and halogen atom include the same groups as those described above.

Examples of the alkyl group and halogen atom in the halogenated alkyl group include the same groups as those described above.

Examples of the condensed polycyclic group include naphthyl, penanthryl and anthryl and the like. Examples of the aralkyloxycarbonyl group include those of which aralkyl portions are various aralkyl groups described above. Examples of the N-alkylcarbamoyl group include those of which alkyl portions are various alkyl groups described above.

Examples of the dialkylamino group include those of which alkyl portions are various alkyl groups described above. Two alkyl groups substituted on the amino may be the same or different.

Examples of the substituent, which may be substituted on each group described above, include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group and the like. The substitution position of the substituent is not specifically limited.

In the present invention, there can be used known electron transferring materials such as benzoquinone compound, malononitrile compound, thiopyran compound, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride, dibromomaleic anhydride, etc., in addition to those described above.

In the present invention, these electron transferring materials may be used alone or in combination thereof.

<Binding Resin>

As the binding resin for dispersing the above respective components, there can be used various resins which have hitherto been used in the photosensitive layer, and examples thereof include thermoplastic resins such as styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin and the like; crosslinking thermosetting resins such as silicone resin, epoxy resin, phenol resin, urea resin, melamine resin and the like; and photosetting resins such as epoxy acrylate, urethane acrylate and the like.

In addition to the above respective components, various additives which have hitherto been known, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors and the like can be formulated in the photosensitive layer as long as the electrophotographic characteristics are not adversely effected by the additives. In order to improve the sensitivity of the photosensitive layer, known sensitizers such as terphenyl, halonaphthoquinones, acenaphthylene and the like may be used in combination with the electric charge generating material.

In the single-layer type photosensitive material, the electric charge generating material is formulated in the amount of 0.1 to 50 parts by weight, and preferably 0.5 to 30 parts by weight, based on 100 parts by weight of the binding resin. The stilbene derivative (1) (hole transferring material) of the present invention is formulated in the amount of 20 to 500 parts by weight, and preferably 30 to 200 parts by weight, based on 100 parts by weight of the binding resin. When the electron transferring material is contained, it is suitable that the amount of the electron transferring material is from 5 to 100 parts by weight, and preferably from 10 to 80 parts by weight, based on 100 parts by weight of the binding resin. The thickness of the photosensitive layer in the single-layer type photosensitive material is from 5 to 100 μm, and preferably from 10 to 50 μm.

The electric charge generating material and binding resin, which constitute the electric charge generating layer, may be used in various proportions in the multi-layer photosensitive material. It is suitable that the electric charge generating material is formulated in the amount of 5 to 1,000 parts by weight, and preferably 30 to 500 parts by weight, based on 100 parts by weight of the binding resin. When a hole transferring material is contained in the electric charge generating layer, it is suitable that the hole transferring material is formulated in the amount of 10 to 500 parts by weight, and preferably 50 to 200 parts by weight, based on 100 parts by weight of the binding resin.

The hole transferring material and binding resin, which constitute the electric charge transferring layer, can be used in various proportions within such a range as not to prevent the transfer of electrons and to prevent the crystallization. It is suitable that the stilbene derivative (1) (hole transferring material) of the present invention is used in the amount of 10 to 500 parts by weight, and preferably 25 to 200 parts by weight, based on 100 parts by weight of the binding resin so as to easily transfer electric charges generated by light irradiation in the electric charge generating layer. When the electron transferring material is contained in the electric charge transferring layer, it is suitable that the electron transferring material is formulated in the amount of 5 to 200 parts by weight, and preferably 10 to 100 parts by weight, based on 100 parts by weight of the binding resin.

Regarding the thickness of the photosensitive layer in the multi-layer type photosensitive layer, the thickness of the electric charge generating layer is from about 0.01 to 5 μm, and preferably from about 0.1 to 3 μm, and that of the electric charge transferring layer is from 2 to 100 μm, and preferably from about 5 to 50 μm.

A barrier layer may be formed in such a range as not to injure the characteristics of the photosensitive material between the conductive substrate and photosensitive layer in the single-layer type photosensitive material, and between the conductive substrate and electric charge generating layer, between the conductive substrate layer and electric charge transferring layer or between the electric charge generating layer and electric charge transferring layer in the multi-layer type photosensitive material. Further, a protective layer may be formed on the surface of the photosensitive layer.

As the conductive substrate to be used in the electrophotosensitive material of the present invention, various materials having the conductivity can be used. Examples of the conductive substrate include single metals such as iron, aluminum, copper, tin, platinum, silver, vanadium, molybdenum, chromium, cadmium, titanium, nickel, palladium, indium, stainless steel, brass and the like; plastic materials which are vapor-deposited or laminated with the above metal; glass materials coated with aluminum iodide, tin oxide, indium oxide and the like.

The conductive substrate may be made in a form of a sheet or a drum according to a structure of the image forming device to be used. The substrate itself may have a conductivity or only the surface of the substrate may have a conductivity. It is preferred that the conductive substrate has sufficient mechanical strength when used.

When the above photosensitive layer is formed by the application method, the above electric charge generating material, electric charge transferring material and binding resin may be dispersed and mixed together with a suitable solvent by using a known method such as a roll mill, a ball mill, an atriter, a paint shaker, a supersonic dispenser, etc. to prepare a dispersion which is applied by using a known means and then allowed to dry.

As the solvent for preparing the coating solution, there can be used various organic solvents, and examples thereof include alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, chloroform, carbon tetrachloride, chlorobenzene and the like; ethers such as dimethyl ether, diethyl ether, tetrahydrofuran, ethylene glycol dimethyl ether, diethylene glycol dimethyl ether and the like; ketones such as acetone, methyl ethyl ketone, cyclohexanone and the like; esters such as ethyl acetate, methyl acetate and the like; dimethylformaldehyde, dimethylformamide, dimethyl sulfoxide, and the like. These solvents may be used alone or in combination thereof.

In order to improve the dispersibility of the electric charge transferring material and electric charge generating material as well as the smoothness of the surface of the photosensitive layer, there may be used surfactants, leveling agents or the like.

EXAMPLES

The following Synthesis Examples, Examples and Comparative Examples further illustrate the present invention in detail.

Synthesis of Stilbene Derivative

Reference Example 1

Synthesis of 2,6-dimethyltriphenylamine 2,6-dimethylaniline (15 g, 124 mmol), iodobenzene (50 g, 245 mmol), anhydrous potassium carbonate (17 g, 123 mmol) and powdered copper (1 g, 16 mmol) were added in 150 ml of nitrobenzene, and the mixture was reacted under reflux for about 24 hours. After the completion of the reaction, the inorganic salt was removed and the solvent was distilled off. The resulting residue was purified by silica gel column chromatography (developing solvent: chloroform/hexane mixed solvent) to obtain 28.8 g of the titled compound (yield: 85%).

Reference Example 2

Synthesis of 2-ethyl-6 -methyltriphenylamine

According to the same manner as that described in Reference Example 1 except for using the same molar amount of 6-ethyl-o-toluidine in place of 2,6-dimethylaniline, the reaction was performed to obtain 28.1 g of the titled compound (yield: 79%).

Reference Example 3

Synthesis of 2,6-diethylphenylamine

According to the same manner as that described in Reference Example 1 except for using the same molar amount of 2,6-diethylaniline in place of 2,6-dimethylaniline, the reaction was performed to obtain 31.0 g of the titled compound (yield: 83%).

Reference Example 4

Synthesis of 2,3-dimethyltriphenylamine

According to the same manner as that described in Reference Example 1 except for using the same molar amount of 2,3-dimethylaniline in place of 2,6-dimethylaniline, the reaction was performed to obtain 28.4 g of the titled compound (yield: 84%).

Reference Example 5

Synthesis of 2-ethyltriphenylamine

According to the same manner as that described in Reference Example 1 except for using the same molar amount of 2-ethylaniline in place of 2,6-dimethylaniline, the reaction was performed to obtain 26.7 g of the titled compound (yield: 79%).

Reference Example 6

Synthesis of 2,6-dimethyl-4'-formyltriphenylamine 2,6-dimethyltriphenylamine (28 g, 102 mmol) was dissolved in 300 ml of dimethylformamide (DMF) and phosphoric acid oxychloride (16 g, 104 mmol) was added, and the mixture was reacted at 40° C. for 1 hour. After the completion of the reaction, the reaction solution was added in 300 ml of water and extracted with ethyl acetate. The organic layer was washed with water and dried to distill off the solvent. Then, the residue was purified by silica gel column chromatography (developing solvent: chloroform/hexane mixed solvent) to obtain 26.8 g of the titled compound (yield: 87%).

Reference Example 7

Synthesis of 2-ethyl-6-methyl-4'-formyltriphenylamine

According to the same manner as that described in Reference Example 6 except for using the same molar amount of 2-ethyl-6-methyltriphenylamine in place of 2,6-dimethyltriphenylamine, the reaction was performed to obtain 28.2 g of the titled compound (yield: 87%).

Reference Example 8

Synthesis of 2,6-diethyl-4'-formyltriphenylamine

According to the same manner as that described in Reference Example 6 except for using the same molar amount of 2,6-diethyltriphenylamine in place of 2,6-dimethyltriphenylamine, the reaction was performed to obtain 27.1 g of the titled compound (yield: 80%).

Reference Example 9

Synthesis of 2,3-dimethyl-4'-formyltriphenylamine

According to the same manner as that described in Reference Example 6 except for using the same molar amount of 2,3-dimethyltriphenylamine in place of 2,6-dimethytriphenylamine, the reaction was performed to obtain 27.5 g of the titled compound (yield: 89%).

Reference Example 10

Synthesis of 2-ethyl-4'-formyltriphenylamine

According to the same manner as that described in Reference Example 6 except for using the same molar amount of 2-ethyltriphenylamine in place of 2,6-dimethyltriphenylamine, the reaction was performed to obtain 24.8 g of the titled compound (yield: 80%).

Reference Example 11

Synthesis of bisphosphate

A bisphosphate derivative represented by the following formula (3p) was obtained from triethyl phosphate and p-xylene dichloride. Furthermore, a bisphosphate derivative represented by the following formula (3 m) was obtained from triethyl phosphate and m-xylylene dichloride.

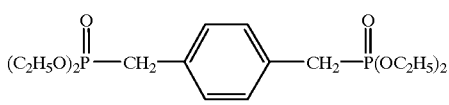

(3p)

-continued

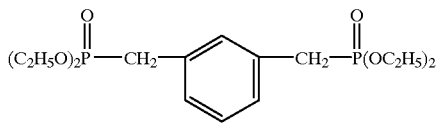

(3m)

Reference Example 12

Synthesis of 2-methoxytriphenylamine 2-methoxytriphenylamine can be obtained by performing the reaction described in Reference Example 1 except for using the same molar amount of o-anisidine in place of 2,6-dimethylaniline.

Reference Example 13

Synthesis of 2-ethoxytriphenylamine 2-ethoxytriphenylamine can be obtained by performing the reaction described in Reference Example 1 except for using the same molar amount of o-phenetidine in place of 2,6-dimethylaniline.

Reference Example 14

Synthesis of 2-methoxy-6-methyl-triphenylamine 2-methoxy-6-methyl-triphenylamine can be obtained by performing the reaction described in Reference Example 1 except for using the same molar amount of 2-methoxy-6-methylaniline in place of 2,6-dimethylaniline.

Reference Example 15

Synthesis of 2-methoxy-5-methyl-triphenylamine 2-methoxy-5-methyl-triphenylamine can be obtained by performing the reaction described in Reference Example 1 except for using the same molar amount of 2-methoxy-5-methylaniline in place of 2,6-dimethylaniline.

Reference Example 16

Synthesis of 5-methoxy-2-methyl-triphenylamine 5-methoxy-2-methyl-triphenylamine can be obtained by performing the reaction described in Reference Example 1 except for using the same molar amount of 5-methoxy-2-methylaniline in place of 2,6-dimethylaniline.

Reference Example 17

Synthesis of 2-methoxy-4'-formiltriphenylamine 2-methoxy-4'-formiltriphenylamine can be obtained by performing the reaction described in Reference Example 6 except for using the same molar amount of 2-methoxytriphenylamine in place of 2,6-dimethyltriphenylamine.

Reference Example 18

Synthesis of 2-ethoxy-4'-formiltriphenylamine 2-ethoxy-4'-formiltriphenylamine can be obtained by performing the reaction described in Reference Example 6 except for using the same molar amount of 2-ethoxytriphenylamine place of 2,6-dimethyltriphenylamine.

Reference Example 19

Synthesis of 2-methoxy-6-methyl-formiltriphenylamine 2-methoxy-6-methyl-formiltriphenylamine can be obtained by performing the reaction described in Reference Example 6 except for using the same molar amount of 5-methoxy-6-methyl-triphenylamine in place of 2,6-dimethylaniline.

Reference Example 20

Synthesis of 2-methoxy-5-methyl-4'-formiltriphenylamine 2-methoxy-5-methyl-4'-formiltriphenylamine can be obtained by performing the reaction described in Reference Example 6 except for using the same molar amount of 2-methoxy-5-methyl-triphenylamine in place of 2,6-dimethyltriphenylamine.

Reference Example 21

Synthesis of 5-methoxy-2-methyl-4'-formiltriphenylamine 5-methoxy-2-methyl-4'-formiltriphenylamine can be obtained by performing the reaction described in Reference Example 6 except for using the same molar amount of 5-methoxy-2-methyl-triphenylamine in place of 2,6-dimethyltriphenylamine.

Synthesis Example 1

Synthesis of stilbene derivative (11-2)

Bisphosphate (5.9 g, 15.6 mmol) represented by the above formula (3p) and sodium hydride dried under deaeration (0.75 g, 31.2 mmol) were added in 200 ml of tetrahydrofuran, followed by ice-cooling. To this mixture, a solution obtained by dissolving 2,6-dimethyl-4'-formyltriphenylamine (9.5 g, 31.5 mmol) in 50 ml of tetrahydrofuran was added dropwise and the reaction was performed at room temperature for about 3 hours. After the completion of the reaction, the reaction solution was added to 400 ml of an aqueous diluted hydrochloric acid solution (about 2%). The deposited crystal was collected by filtration, and then washed with water. The crystal was dried and purified by silica gel column chromatography (developing solvent: chloroform/hexane mixed solvent) to obtain 7.0 g of a stilbene derivative represented by the compound number 11-2 in the above Table 1 (yield: 66%)

Melting point: 190–192° C.

Figure 2:
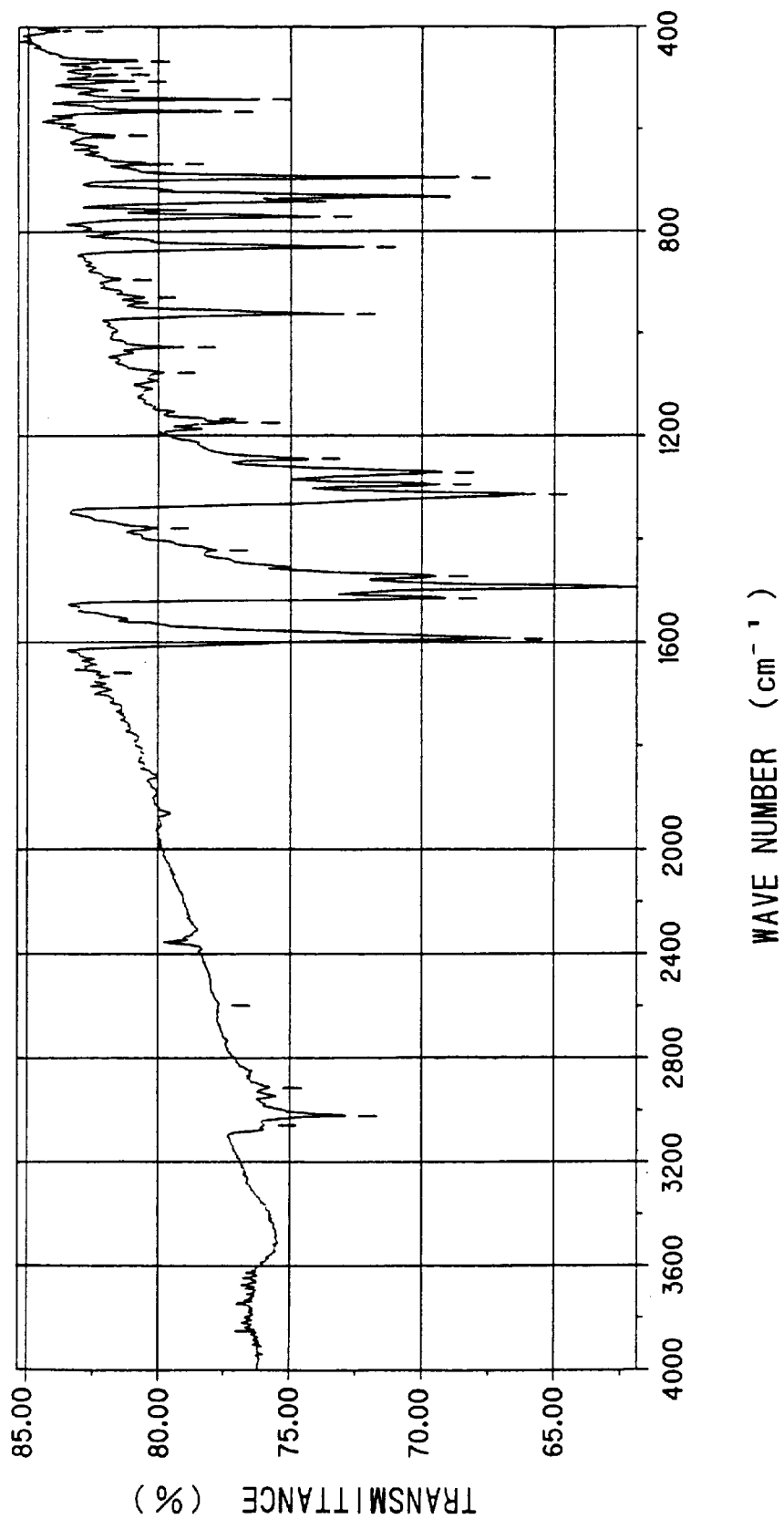
FIG. 2 is a graph illustrating an infrared absorption spectrum of the above stilbene derivative (11-2).

The $^1$H-NMR spectrum of the above stilbene derivative (11-2) is shown in FIG. 1 and the infrared absorption spectrum is shown in FIG. 2.

Synthesis Example 2

Synthesis of stilbene derivative (11-6)

According to the same manner as that described in Synthesis Example 1 except for using the same molar amount of 2-ethyl-6-methyl-4'-formyltriphenylamine in place of 2,6-dimethyl-4'-formyltriphenylamine, the reaction was performed to obtain 7.2 g of a stilbene derivative represented by the compound number 11-6 in the above Table 1 (yield: 65%)

Melting point: 194–197° C.

Figure 3:
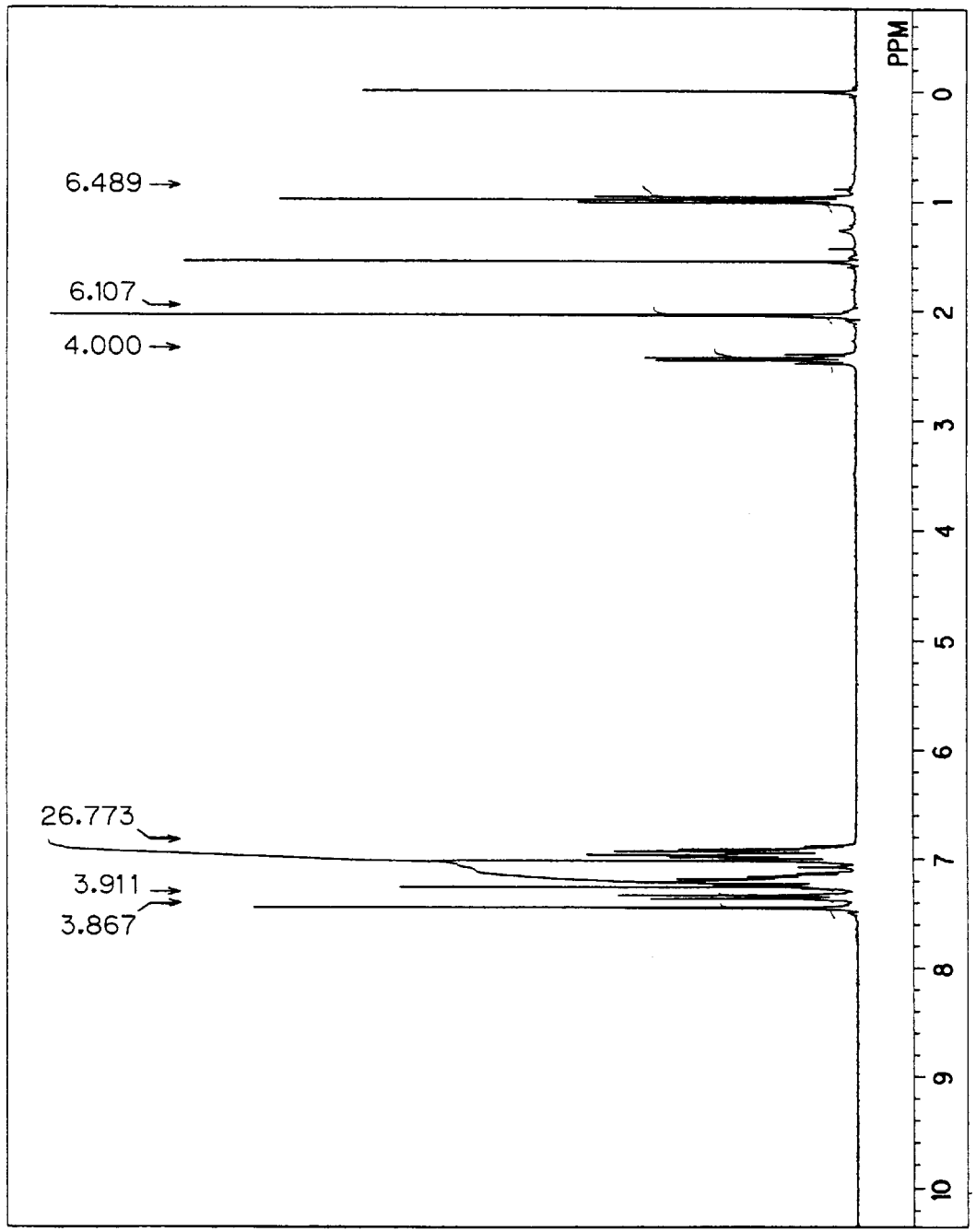
FIG. 3 is a graph illustrating a $^1$H-NMR spectrum of a stilbene derivative (11-6) obtained in Synthesis Example 2.
Figure 4:
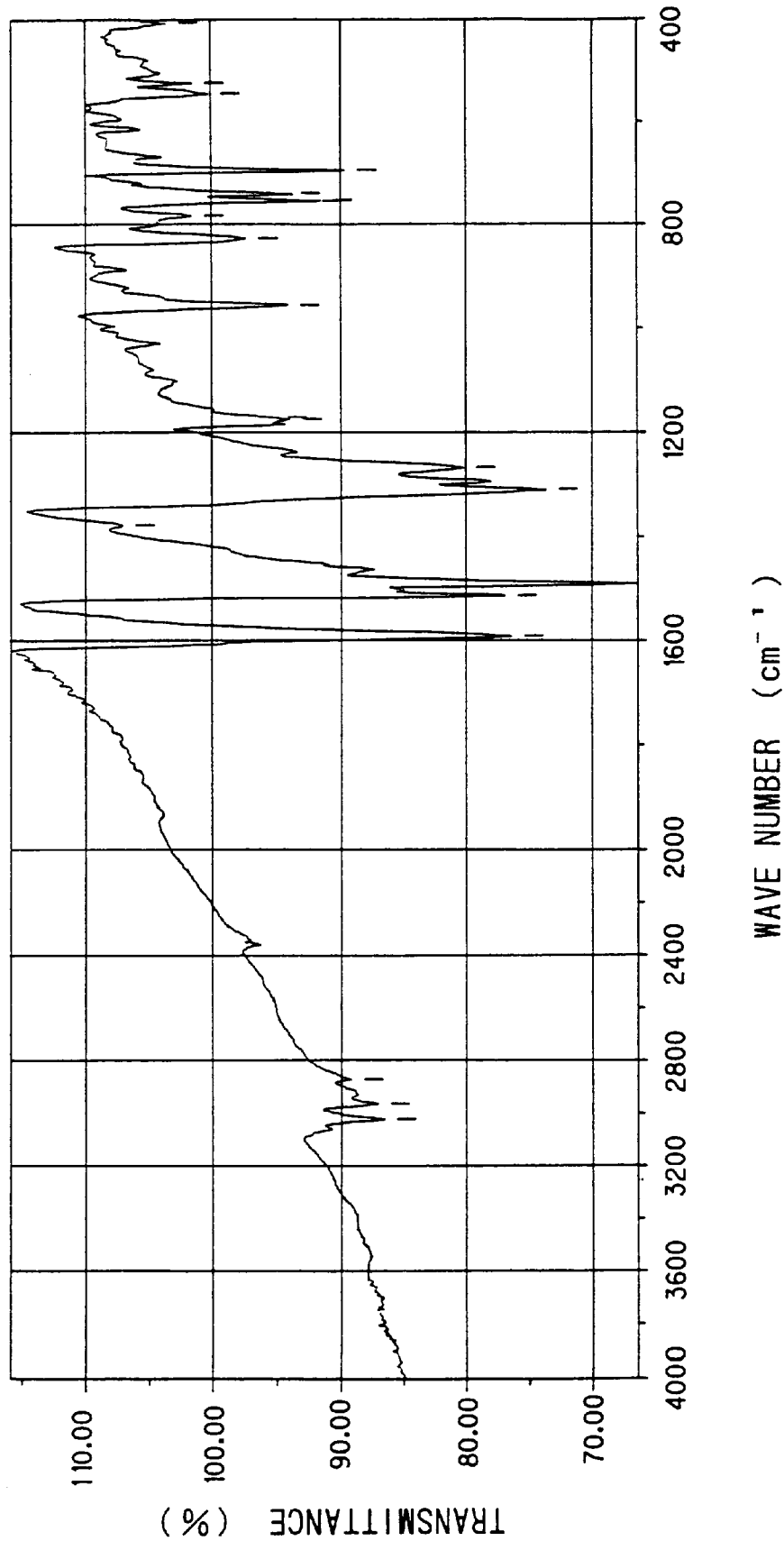
FIG. 4 is a graph illustrating an infrared absorption spectrum of the above stilbene derivative (11-6).

The $^1$H-NMR spectrum of the above stilbene derivative (11-6) is shown in FIG. 3 and the infrared absorption spectrum is shown in FIG. 4.

Synthesis Example 3

Synthesis of stilbene derivative (11-7)

According to the same manner as that described in Synthesis Example 1 except for using the same molar amount of 2,6-diethyl-4'-formyltriphenylamine in place of 2,6-dimethyl-4'-formyltriphenylamine, the reaction was performed to obtain 8.1 g of a stilbene derivative represented by the compound number 11-7 in the above Table 1 (yield: 70%)

Melting point: 224–226° C.

Figure 5:
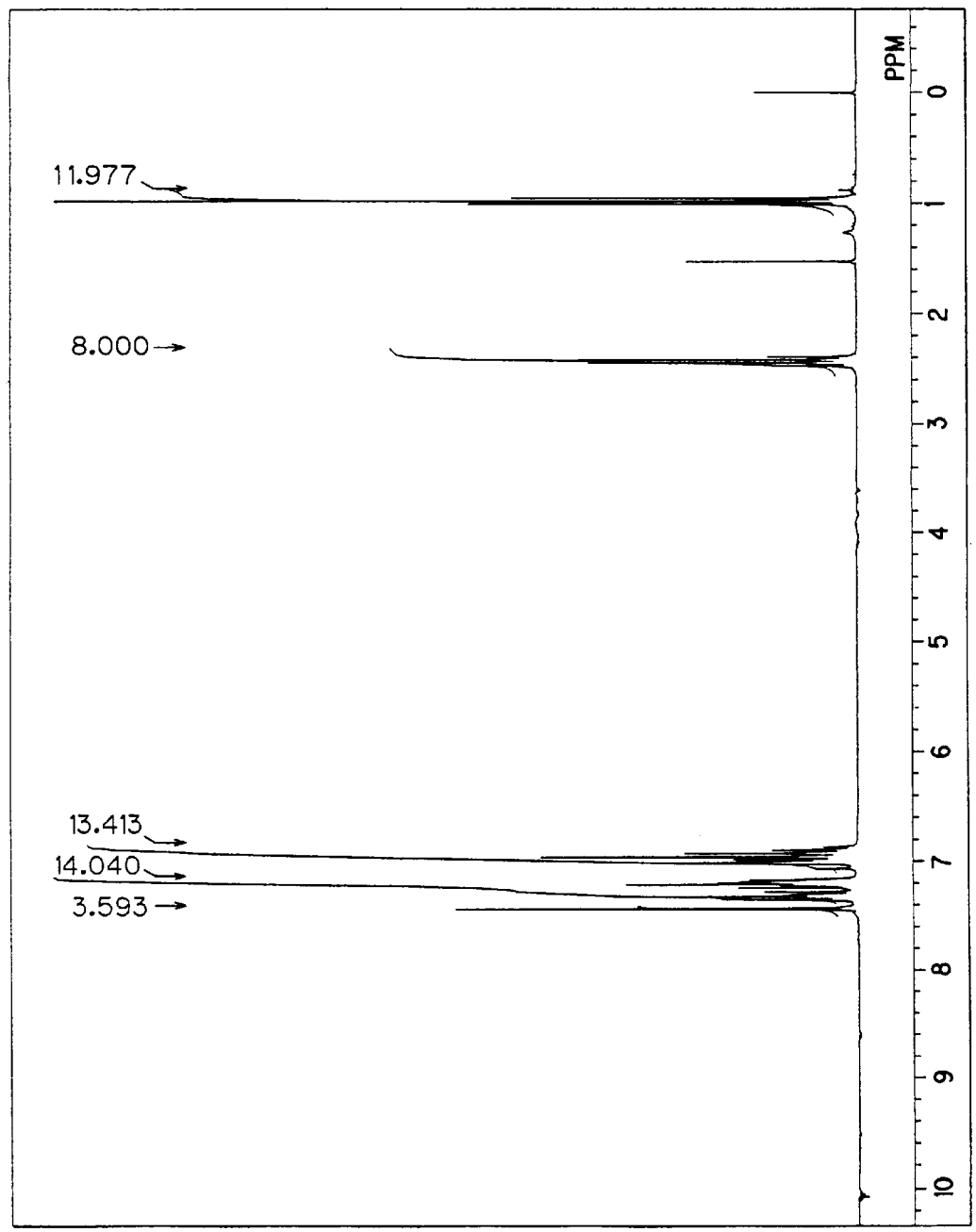
FIG. 5 is a graph illustrating a $^1$H-NMR spectrum of a stilbene derivative (11-7) obtained in Synthesis Example 3.
Figure 6:
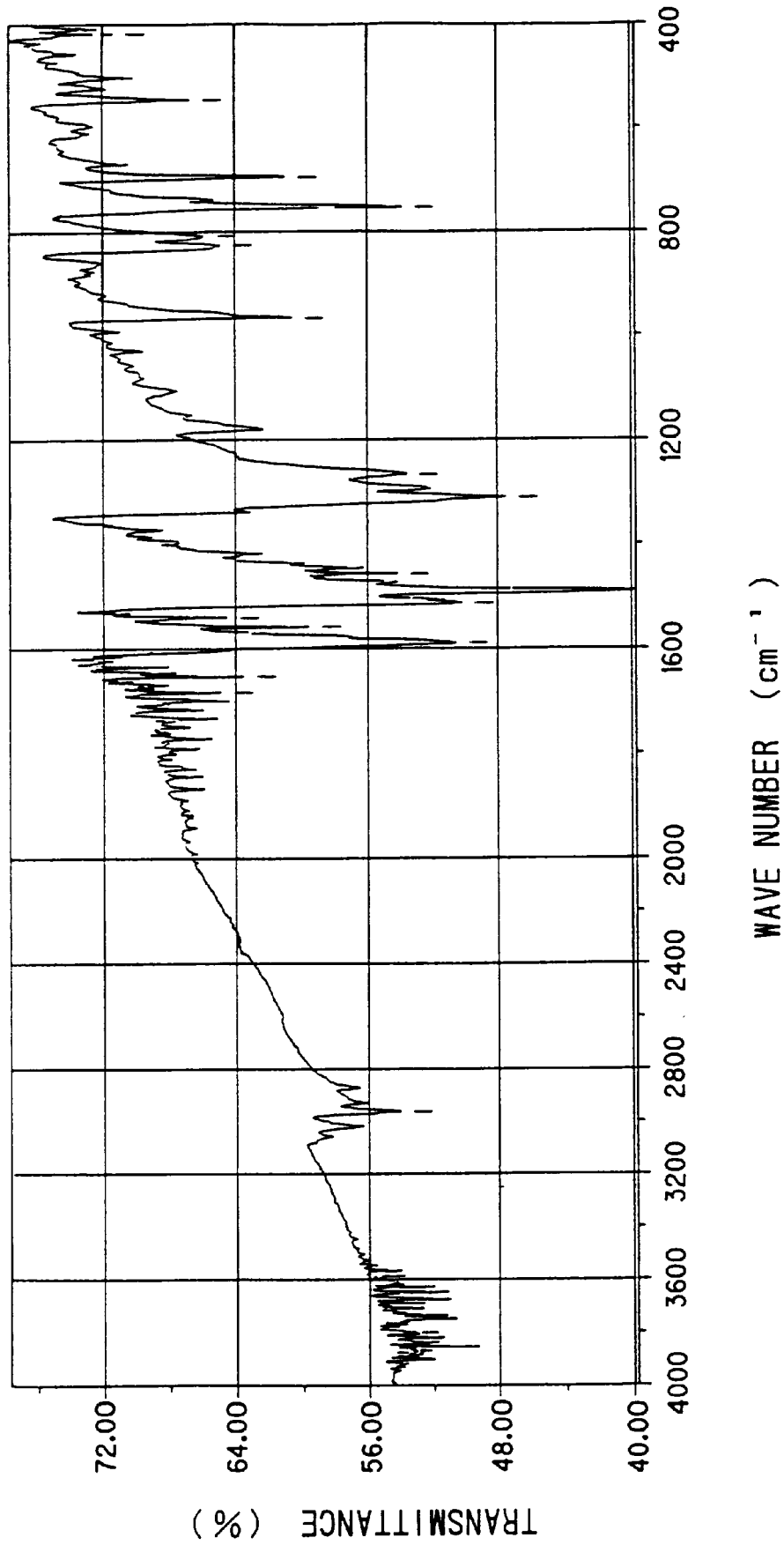
FIG. 6 is a graph illustrating an infrared absorption spectrum of the above stilbene derivative (11-7).

The $^1$H-NMR spectrum of the above stilbene derivative (11-7) is shown in FIG. 5 and the infrared absorption spectrum is shown in FIG. 6.

Synthesis Example 4

Synthesis of stilbene derivative (12-3)

According to the same manner as that described in Synthesis Example 1 except for using the same molar amount of 2,3-dimethyl-4'-formyltriphenylamine in place of 2,6-dimethyl-4'-formyltriphenylamine and using the same molar amount of bisphosphate represented by the above formula (3 m) in place of bisphosphate represented by the above formula (3 p), the reaction was performed to obtain 6.5 g of a stilbene derivative represented by the compound number 12-3 in the above Table 2 (yield: 61%)

Melting point: 93–96° C.

Figure 7:
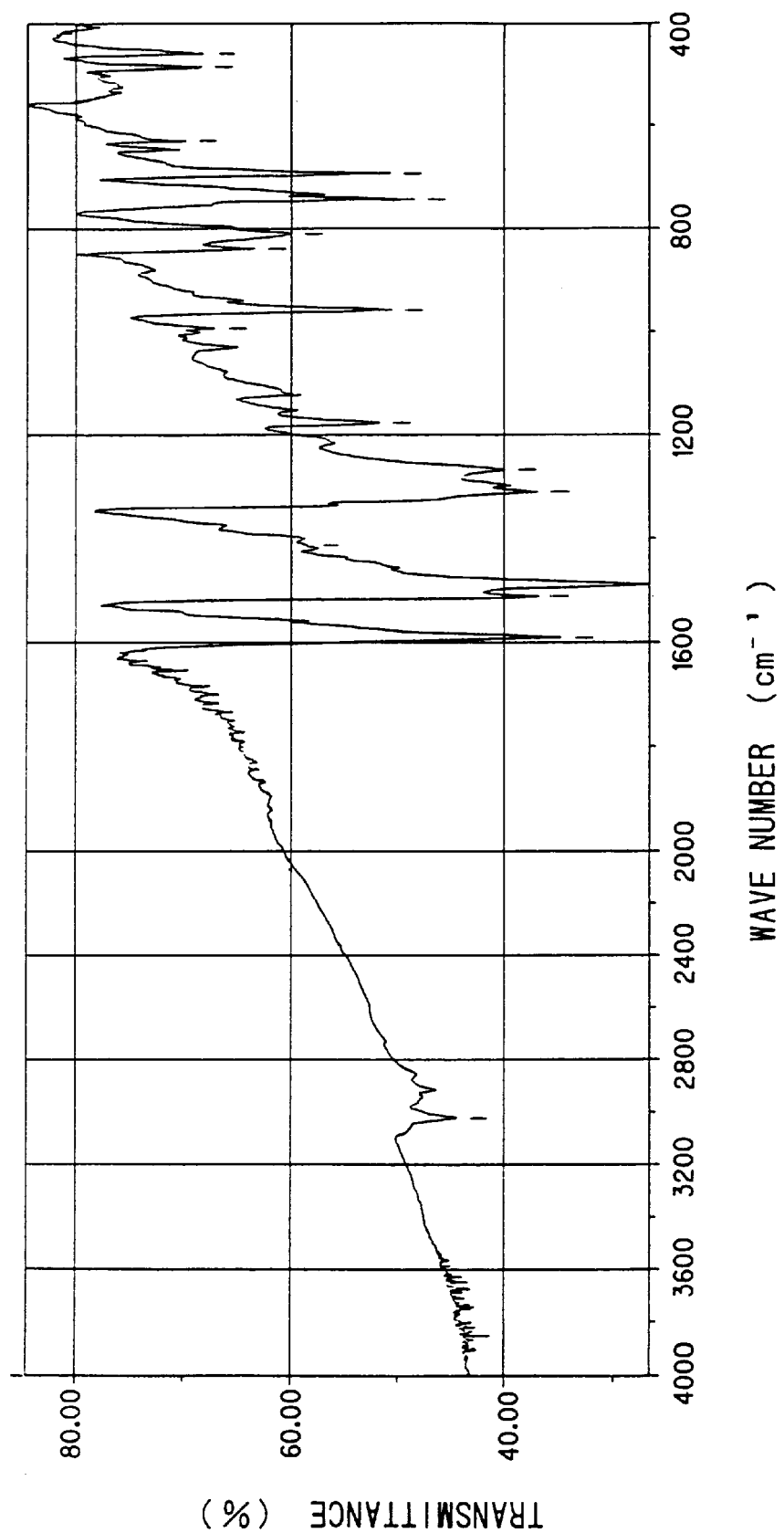
FIG. 7 is a graph illustrating an infrared absorption spectrum of a stilbene derivative (12-3) obtained in Synthesis Example 4.

The infrared absorption spectrum of the above stilbene derivative (12-3) is shown in FIG. 7.

Synthesis Example 5

Synthesis of stilbene derivative (12-5)

According to the same manner as that described in Synthesis Example 1 except for using the same molar amount of 2-ethyl-4'-formyltriphenylamine in place of 2,6-dimethyl-4'-formyltriphenylamine and using the same molar amount of bisphosphate represented by the above formula (3 m) in place of bisphosphate resented by the above general formula (3 p), the reaction was performed to obtain 5.9 g of a stilbene derivative represented by the compound number 12-5 in the above Table 2 (yield: 56%)

Melting point: 92–95° C.

Figure 8:
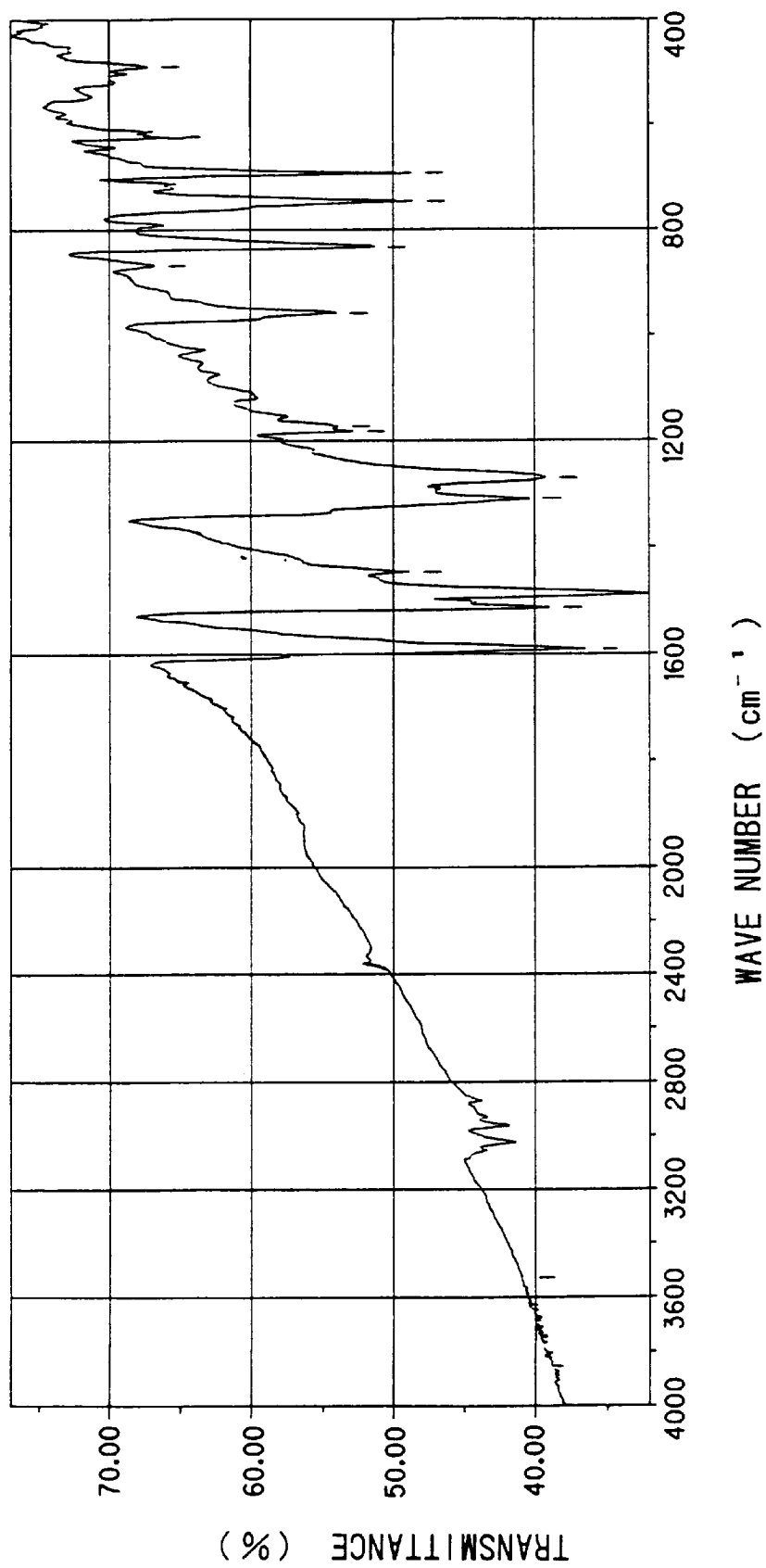
FIG. 8 is a graph illustrating an infrared absorption spectrum of a stilbene derivative (12-5) obtained in Synthesis Example 5.

The infrared absorption spectrum of the above stilbene derivative (12-5) is shown in FIG. 8.

Production of Electrophotosensitive Material (Single-layer type photosensitive material for digital light source)

Synthesis Example 6

Synthesis of stilbene derivative (11-14)

A stilbene derivative represented by the compound number 11-14 in the above Table 1 can be obtained by performing the reaction described in Synthesis Example 1 except for using the same molar amount of 2-methoxy-4'-formyltriphenylamine in place of 2,6-dimethyl-4'-formyltriphenylamine.

Synthesis Example 7

Synthesis of stilbene derivative (11-15)

A stilbene derivative represented by the compound number 11-15 in the above Table 1 can be obtained by performing the reaction described in Synthesis Example 1 except for using the same molar amount of 2-ethoxy-4'-formyltriphenylamine in place of 2,6-dimethyl-4'-formyltriphenylamine.

Synthesis Example 8

Synthesis of stilbene derivative (11-16)

A stilbene derivative represented by the compound number 11-16 in the above Table 1 can be obtained by performing the reaction described in Synthesis Example 1 except for using the same molar amount of 2-methoxy-6-methyl-4'-formyltriphenylamine in place of 2,6-dimethyl-4'-formyltriphenylamine.

Synthesis Example 9

Synthesis of stilbene derivative (11-17)

A stilbene derivative represented by the compound number 11-17 in the above Table 1 can be obtained by performing the reaction described in Synthesis Example 1 except for using the same molar amount of 2-methoxy-5-methyl-4'-formyltriphenylamine in place of 2,6-dimethyl-4'-formyltriphenylamine.

Synthesis Example 10

Synthesis of stilbene derivative (11-18)

A stilbene derivative represented by the compound number 11-18 in the above Table 1 can be obtained by performing the reaction described in Synthesis Example 1 except for using the same molar amount of 5-methoxy-2-methyl-4'-formyltriphenylamine in place of 2,6-dimethyl-4'-formyltriphenylamine.

Synthesis Example 11

Synthesis of stilbene derivative (12-14)

A stilbene derivative represented by the compound number 12-14 in the above Table 2 can be obtained by performing the reaction described in Synthesis Example 1 except for using the same molar amount of 2-methoxy-4'-formyltriphenylamine in place of 2,6-dimethyl-4'-formyltriphenylamine and for using the same molar amount of bisphosphate represented by the above formula (3 m) in place of bisphosphate resented by the above general formula (3 p).

Synthesis Example 12

Synthesis of stilbene derivative (12-15)

A stilbene derivative represented by the compound number 12-15 in the above Table 2 can be obtained by performing the reaction described in Synthesis Example 1 except for using the same molar amount of 2-ethoxy-4'-formyltriphenylamine in place of 2,6-dimethyl-4'- formyltriphenylamine and for using the same molar amount of bisphosphate represented by the above formula (3 m) in place of bisphosphate resented by the above general formula (3 p).

Synthesis Example 13

Synthesis of stilbene derivative (12-16)

A stilbene derivative represented by the compound number 12-16 in the above Table 2 can be obtained by performing the reaction described in Synthesis Example 1 except for using the same molar amount of 2-methoxy-6-methyl-4'-formyltriphenylamine in place of 2,6-dimethyl-4'-formyltriphenylamine and for using the same molar amount of bisphosphate represented by the above formula (3 m) in place of bisphosphate resented by the above general formula (3 p).

Synthesis Example 14

Synthesis of stilbene derivative (12-17)

A stilbene derivative represented by the compound number 12-17 in the above Table 2 can be obtained by performing the reaction described in Synthesis Example 1 except for using the same molar amount of 2-methoxy-5-methyl-4'-formyltriphenylamine in place of 2,6-dimethyl-4'-formyltriphenylamine and for using the same molar amount of bisphosphate represented by the above formula (3 m) in place of bisphosphate resented by the above general formula (3 p).

Synthesis Example 15

Synthesis of stilbene derivative (12-18)

A stilbene derivative represented by the compound number 12-18 in the above Table 2 can be obtained by perfoming the reaction described in Synthesis Example 1 except for using the same molar amount of 5-methoxy-2-methyl-4'-formyltriphenylamine in place of 2,6-dimethyl-4'-formyltriphenylamine and for using the same molar amount of bisphosphate represented by the above formula (3 m) in place of bisphosphate resented by the above general formula (3 p).

Examples 1

An X type metal-free phthalocyanine (CG1-1) was used as the electric charge generating material. A stilbene derivative represented by the compound number (11-2) of the above Table 1 was used as the hole transferring material.

5 Parts by weight of the above electric charge generating material, 100 parts by weight of the above hole transferring material and 100 parts by weight of a binding resin (polycarbonate) were mixed and dispersed, together with 800 parts by weight of a solvent (tetrahydrofuran), in a ball mill for 50 hours to prepare a coating solution for single-layer type photosensitive layer.

Then, this coating solution was applied on a conductive substrate (aluminum tube) by using the dip coating method, followed by hot-air drying at 100° C. for 30 minutes to obtain a single-layer type photosensitive material for digital light source, which has a single-layer type photosensitive layer of 25 μm in film thickness.

Example 2

According to the same manner as that described in Example 1 except for using a stilbene derivative represented by the compound number (11-6) of the above Table 1 as the hole transferring material, a single-layer type photosensitive material for digital light source was produced.

Example 3

According to the same manner as that described in Example 1 except for using a stilbene derivative represented by the compound number (11-7) of the above Table 1 as the hole transferring material, a single-layer type photosensitive material for digital light source was produced.

Example 4

According to the same manner as that described in Example 1 except for using a stilbene derivative represented by the compound number (12-3) of the above Table 1 as the hole transferring material, a single-layer type photosensitive material for digital light source was produced.

Example 5

According to the same manner as that described in Example 1 except for using a stilbene derivative represented by the compound number (12-5) of the above Table 1 as the hole transferring material, a single-layer type photosensitive material for digital light source was produced.

Example 6

According to the same manner as that described in Example 1 except for further formulating 30 parts by weight of a diphenoquinone derivative represented by the formula (ET17-1):

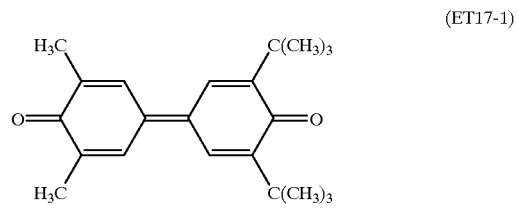

(ET17-1)

as the electron transferring material in the coating solution for single-layer photosensitive layer, a single-layer type photosensitive material for digital light source was produced.

Example 7

According to the same manner as that described in Example 6 except for using a stilbene derivative represented by the compound number (11-6) as the hole transferring material, a single-layer type photosensitive material for digital light source was produced.

Example 8

According to the same manner as that described in Example 6 except for using a stilbene derivative represented by the compound number (11-7) as the hole transferring material, a single-layer type photosensitive material for digital light source was produced.

Example 9

According to the same manner as that described in Example 6 except for using a stilbene derivative represented by the compound number (12-3) as the hole transferring material, a single-layer type photosensitive material for digital light source was produced.

Example 10

According to the same manner as that described in Example 6 except for using a stilbene derivative represented by the compound number (12-5) as the hole transferring material, a single-layer type photosensitive material for digital light source was produced.

Examples 11 to 15

According to the same manner as that described in Examples 6 to 10 except for using a naphthoquinone derivative represented by the formula (ET14-1):

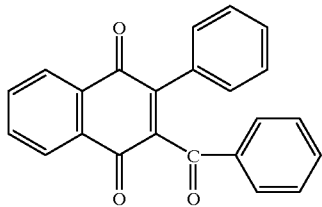

(ET14-1)

as the electron transferring material, single-layer type photosensitive materials for digital light source were produced, respectively.

Examples 16 to 20

According to the same manner as that described in Examples 6 to 10 except for using a naphthoquinone derivative represented by the formula (ET14-2):

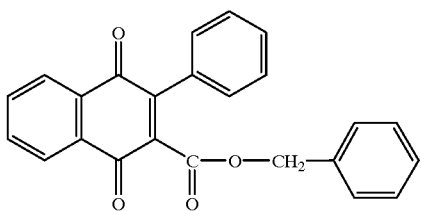

(ET14-2)

as the electron transferring material, single-layer type photosensitive materials for digital light source were produced, respectively.

Comparative Example 1

According to the same manner as that described in Example 1 except for using a stilbene derivative represented by the formula (6-1):

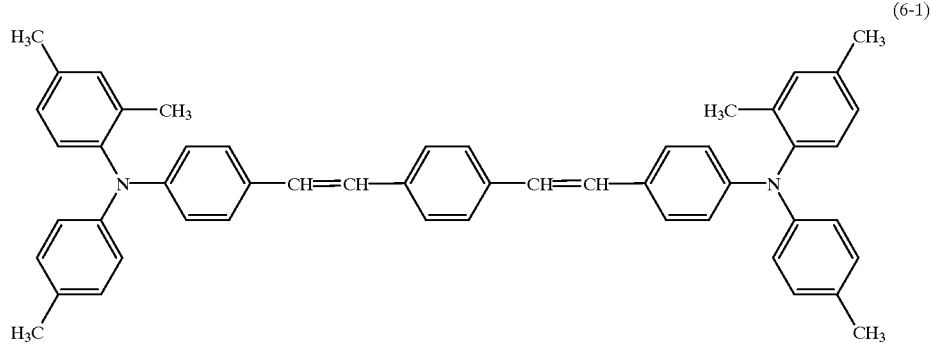

(6-1)

as the hole transferring material, a single-layer type photosensitive material for digital light source was produced, respectively.

Comparative Example 2

According to the same manner as that described in Example 1 except for using a stilbene derivative represented by the formula (6-2):

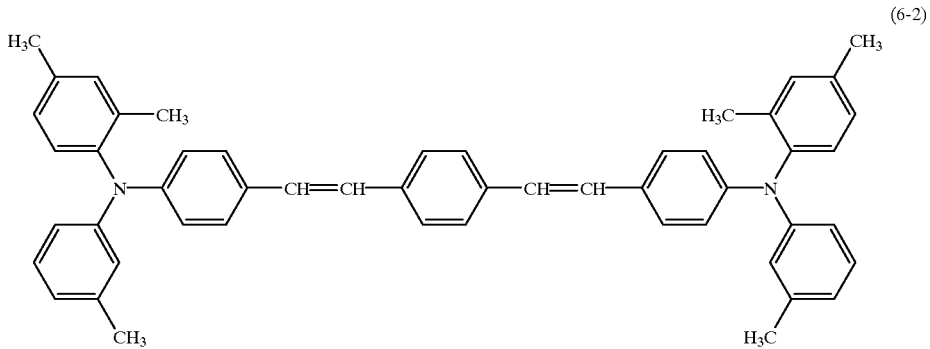

(6-2)

as the hole transferring material, a single-layer type photosensitive material for digital light source was produced, respectively.

Comparative Example 3

According to the same manner as that described in Example 1 except for using a stilbene derivative represented by the formula (6-3):

The kind of the electric charge generating material, hole transferring material and electron transferring material used in the above respective Examples and Comparative Examples as well as test results of the electrical characteristics are shown in Table 3. In the following tables, the electric charge generating material, hole transferring material and electron transferring material were represented by each formula number or each compound number.

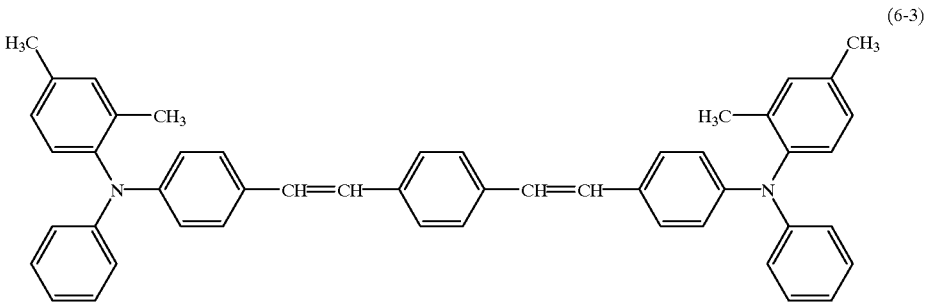

(6-3)

as the hole transferring material, a single-layer type photosensitive material for digital light source was produced, respectively.

The photosensitive materials obtained in Examples 1 to 20 and Comparative Examples 1 to 3 were subjected to the following electrical characteristics test (I) and the electrical characteristics of the respective photosensitive materials were evaluated.

Electrical characteristics test (1)

By using a drum sensitivity tester manufactured by GEN-TEC Co., a voltage was applied on the surface of each photosensitive material to charge the surface at +700 V±20 V and the surface potential $V_0$ (V) was measured. Then, monochromatic light [wavelength: 780 nm (half-width: 20 nm), light intensity: 8 $\mu J/cm^2$] from white light of a halogen lamp as an exposure light source through a band-pass filter was irradiated on the surface of each photosensitive material (irradiation time: 1.5 sec.) and the time required to reduce the above surface potential $V_0$ to half was measured and a half-time exposure $E_{1/2}$ ($\mu J/cm^2$) was calculated. Further, a surface potential at the time at which 0.5 sec. has passed since the beginning of exposure was measured as a residual potential $V_r$ (V).

TABLE 3

| | Electric charge generating material | Hole transferring material | Electron transferring material | $V_o$ | $V_r$ | $E_{1/2}$ |
|---|---|---|---|---|---|---|
| Example 1 | CG 1-1 | 11-2 | — | 700 | 113 | 0.73 |
| Example 2 | CG 1-1 | 11-6 | — | 701 | 114 | 0.74 |
| Example 3 | CG 1-1 | 11-7 | — | 698 | 112 | 0.73 |
| Example 4 | CG 1-1 | 12-3 | — | 698 | 117 | 0.75 |
| Example 5 | CG 1-1 | 12-5 | — | 700 | 116 | 0.75 |
| Example 6 | CG 1-1 | 11-2 | ET17-1 | 704 | 92 | 0.67 |
| Example 7 | CG 1-1 | 11-6 | ET17-1 | 703 | 94 | 0.68 |
| Example 8 | CG 1-1 | 11-7 | ET17-1 | 706 | 92 | 0.67 |
| Example 9 | CG 1-1 | 12-3 | ET17-1 | 704 | 97 | 0.69 |
| Example 10 | CG 1-1 | 12-5 | ET17-1 | 700 | 96 | 0.68 |
| Example 11 | CG 1-1 | 11-2 | ET14-1 | 701 | 96 | 0.68 |
| Example 12 | CG 1-1 | 11-6 | ET14-1 | 697 | 96 | 0.69 |
| Example 13 | CG 1-1 | 11-7 | ET14-1 | 699 | 97 | 0.69 |
| Example 14 | CG 1-1 | 12-3 | ET14-1 | 700 | 104 | 0.72 |
| Example 15 | CG 1-1 | 12-5 | ET14-1 | 704 | 103 | 0.72 |
| Example 16 | CG 1-1 | 11-2 | ET14-2 | 705 | 90 | 0.66 |
| Example 17 | CG 1-1 | 11-6 | ET14-2 | 704 | 91 | 0.66 |
| Example 18 | CG 1-1 | 11-7 | ET14-2 | 700 | 89 | 0.66 |
| Example 19 | CG 1-1 | 12-3 | ET14-2 | 699 | 99 | 0.69 |
| Example 20 | CG 1-1 | 12-5 | ET14-2 | 698 | 100 | 0.70 |
| Comp. Ex. 1 | CG 1-1 | 6-1 | — | 703 | 143 | 0.80 |

TABLE 3-continued

| | Electric charge generating material | Hole transferring material | Electron transferring material | $V_o$ | $V_r$ | $E_{1/2}$ |
|---|---|---|---|---|---|---|
| Comp. Ex. 2 | CG 1-1 | 6-2 | — | 700 | 142 | 0.79 |
| Comp. Ex. 3 | CG 1-1 | 6-3 | — | 695 | 139 | 0.78 |

Examples 21 to 25

According to the same manner as that described in Examples 1 to 5 except for using an α type oxotitanylphthalocyanine (CG2-1) as the electric charge generating material, single-layer type photosensitive materials for digital light source were produced, respectively.

Examples 26 to 30

According to the same manner as that described in Examples 6 to 10 except for using an α type oxotitanylphthalocyanine (CG2-1) as the electric charge generating material, single-layer type photosensitive materials for digital light source were produced, respectively.

Examples 31 to 35

According to the same manner as that described in Examples 11 to 15 except for using an α type oxotitanylphthalocyanine (CG2-1) as the electric charge generating material, single-layer type photosensitive materials for digital light source were produced, respectively.

Examples 36 to 40

According to the same manner as that described in Examples 16 to 20 except for using an α type oxotitanylphthalocyanine (CG2-1) as the electric charge generating material, single-layer type photosensitive materials for digital light source were produced, respectively.

Comparative Examples 4 to 6

According to the same manner as that described in Comparative Examples 1 to 3 except for using an α type oxotitanylphthalocyanine (CG2-1) as the electric charge generating material, single-layer type photosensitive materials for digital light source were produced, respectively.

The photosensitive materials obtained in Examples 21 to 40 and Comparative Examples 4 to 6 were subjected to the above electrical characteristics test (I) and the electrical characteristics of the respective photosensitive materials were evaluated. The kind of the electric charge generating material, hole transferring material and electron transferring material used in the above respective Examples and Comparative Examples as well as test results of the electrical characteristics are shown in Table 4.

TABLE 4

| | Electric charge generating material | Hole transferring material | Electron transferring material | $V_o$ | $V_r$ | $E_{1/2}$ |
|---|---|---|---|---|---|---|
| Example 21 | CG 2-1 | 11-2 | — | 702 | 112 | 0.74 |
| Example 22 | CG 2-1 | 11-6 | — | 704 | 114 | 0.74 |
| Example 23 | CG 2-1 | 11-7 | — | 690 | 111 | 0.73 |
| Example 24 | CG 2-1 | 12-3 | — | 698 | 116 | 0.75 |
| Example 25 | CG 2-1 | 12-5 | — | 699 | 117 | 0.75 |
| Example 26 | CG 2-1 | 11-2 | ET17-1 | 704 | 93 | 0.67 |
| Example 27 | CG 2-1 | 11-6 | ET17-1 | 703 | 94 | 0.67 |
| Example 28 | CG 2-1 | 11-7 | ET17-1 | 705 | 92 | 0.67 |
| Example 29 | CG 2-1 | 12-3 | ET17-1 | 705 | 97 | 0.68 |
| Example 30 | CG 2-1 | 12-5 | ET14-1 | 698 | 98 | 0.69 |
| Example 31 | CG 2-1 | 11-2 | ET14-1 | 698 | 97 | 0.69 |
| Example 32 | CG 2-1 | 11-6 | ET14-1 | 700 | 99 | 0.70 |
| Example 33 | CG 2-1 | 11-7 | ET14-1 | 704 | 100 | 0.70 |
| Example 34 | CG 2-1 | 12-3 | ET14-1 | 699 | 104 | 0.72 |
| Example 35 | CG 2-1 | 12-5 | ET14-1 | 704 | 101 | 0.70 |
| Example 36 | CG 2-1 | 11-2 | ET14-2 | 705 | 91 | 0.65 |
| Example 37 | CG 2-1 | 11-6 | ET14-2 | 703 | 93 | 0.66 |
| Example 38 | CG 2-1 | 11-7 | ET14-2 | 702 | 92 | 0.66 |
| Example 39 | CG 2-1 | 12-3 | ET14-2 | 700 | 99 | 0.68 |
| Example 40 | CG 2-1 | 12-5 | ET14-2 | 700 | 99 | 0.69 |
| Comp. Ex. 4 | CG 2-1 | 6-1 | — | 701 | 135 | 0.77 |
| Comp. Ex. 5 | CG 2-1 | 6-2 | — | 705 | 140 | 0.80 |
| Comp. Ex. 6 | CG 2-1 | 6-3 | — | 699 | 139 | 0.79 |

Examples 41 to 45

According to the same manner as that described in Examples 1 to 5 except for using a Y type oxotitanylphthalocyanine (CG2-2) as the electric charge generating material, single-layer type photosensitive materials for digital light source were produced, respectively.

Examples 46 to 50

According to the same manner as that described in Examples 6 to 10 except for using a Y type oxotitanylphthalocyanine (CG2-2) as the electric charge generating material, single-layer type photosensitive materials for digital light source were produced, respectively.

Examples 51 to 55

According to the same manner as that described in Examples 11 to 15 except for using a Y type oxotitanylphthalocyanine (CG2-2) as the electric charge generating material, single-layer type photosensitive materials for digital light source were produced, respectively.

Examples 56 to 60

According to the same manner as that described in Examples 16 to 20 except for using a Y type oxotitanylphthalocyanine (CG2-2) as the electric charge generating material, single-layer type photosensitive materials for digital light source were produced, respectively.

Comparative Examples 7 to 9

According to the same manner as that described in Comparative Examples 1 to 3 except for using a Y type oxotitanylphthalocyanine (CG2-2) as the electric charge generating material, single-layer type photosensitive materials for digital light source were produced, respectively.

The photosensitive materials obtained in Examples 41 to 60 and Comparative Examples 7 to 9 were subjected to the above electrical characteristics test (I) and the electrical characteristics of the respective photosensitive materials were evaluated. The kind of the electric charge generating material, hole transferring material and electron transferring material used in the above respective Examples and Comparative Examples as well as test results of the electrical characteristics are shown in Table 5.

TABLE 5

| | Electric charge generating material | Hole transferring material | Electron transferring material | $V_o$ | $V_r$ | $E_{1/2}$ |
|---|---|---|---|---|---|---|
| Example 41 | CG 2-2 | 11-2 | — | 704 | 114 | 0.63 |
| Example 42 | CG 2-2 | 11-6 | — | 700 | 113 | 0.62 |
| Example 43 | CG 2-2 | 11-7 | — | 701 | 113 | 0.63 |
| Example 44 | CG 2-2 | 12-3 | — | 702 | 118 | 0.64 |
| Example 45 | CG 2-2 | 12-5 | — | 700 | 119 | 0.65 |
| Example 46 | CG 2-2 | 11-2 | ET17-1 | 698 | 91 | 0.61 |
| Example 47 | CG 2-2 | 11-6 | ET17-1 | 699 | 93 | 0.61 |
| Example 48 | CG 2-2 | 11-7 | ET17-1 | 697 | 90 | 0.60 |
| Example 49 | CG 2-2 | 12-3 | ET17-1 | 699 | 99 | 0.62 |
| Example 50 | CG 2-2 | 12-5 | ET17-1 | 704 | 100 | 0.62 |
| Example 51 | CG 2-2 | 11-2 | ET14-1 | 703 | 91 | 0.60 |
| Example 52 | CG 2-2 | 11-6 | ET14-1 | 703 | 91 | 0.60 |
| Example 53 | CG 2-2 | 11-7 | ET14-1 | 702 | 93 | 0.61 |
| Example 54 | CG 2-2 | 12-3 | ET14-1 | 700 | 99 | 0.62 |
| Example 55 | CG 2-2 | 12-5 | ET14-1 | 700 | 100 | 0.62 |
| Example 56 | CG 2-2 | 11-2 | ET14-2 | 698 | 87 | 0.59 |
| Example 57 | CG 2-2 | 11-6 | ET14-2 | 698 | 88 | 0.60 |
| Example 58 | CG 2-2 | 11-7 | ET14-2 | 702 | 90 | 0.61 |
| Example 59 | CG 2-2 | 12-3 | ET14-2 | 701 | 95 | 0.62 |
| Example 60 | CG 2-2 | 12-5 | ET14-2 | 697 | 97 | 0.62 |
| Comp. Ex. 7 | CG 2-2 | 6-1 | — | 701 | 130 | 0.79 |
| Comp. Ex. 8 | CG 2-2 | 6-2 | — | 700 | 125 | 0.73 |
| Comp. Ex. 9 | CG 2-2 | 6-3 | — | 705 | 128 | 0.75 |

(Multi-layer type electrophotosensitive material for digital light source)

Example 61

2.5 Parts by weight of a X type metal-free phthalocyanine (CG1-1) as the electric charge generating material and 1 parts by weight of a binding resin (polyvinyl butyral) were mixed and dispersed, together with 15 parts by weight of a solvent (tetrahydrofuran), in a ball mill to prepare a coating solution for electric charge generating layer. Then, this coating solution was applied on a conductive substrate (aluminum tube) by using the dip coating method, followed by hot-air drying at 110° C. for 30 minutes to form an electric charge generating layer of 0.5 μm in film thickness.

Then, 1 part by weight of a stilbene derivative (11-2) as the hole transferring material and 1 part by weight of a binding resin (polycarbonate) were mixed and dispersed, together with 10 parts by weight of a solvent (tetrahydrofuran), in a ball mill to prepare a coating solution for electric charge transferring layer. Then, this coating solution was applied on the above electric charge generating layer by using the dip coating method, followed by hot-air drying at 110° C. for 30 minutes to form an electric charge transferring layer of 20 μm in film thickness, thereby producing a multi-layer type photosensitive material.

Example 62

According to the same manner as that described in Example 61 except for using a stilbene derivative represented by the compound number (11-6) as the hole transferring material, a multi-layer type photosensitive material for digital light source was produced.

Example 63

According to the same manner as that described in Example 61 except for using a stilbene derivative represented by the compound number (11-7) as the hole transferring material, a multi-layer type photosensitive material for digital light source was produced.

Example 64

According to the same manner as that described in Example 61 except for using a stilbene derivative represented by the compound number (12-3) as the hole transferring material, a multi-layer type photosensitive material for digital light source was produced.

Example 65

According to the same manner as that described in Example 61 except for using a stilbene derivative represented by the compound number (12-5) as the hole transferring material, a multi-layer type photosensitive material for digital light source was produced.

Examples 66 to 70

According to the same manner as that described in Examples 61 to 65 except for using an α type oxotitanylphthalocyanine (CG2-1) as the electric charge generating material, multi-layer type photosensitive materials for digital light source were produced, respectively.

Examples 71 to 75

According to the same manner as that described in Examples 61 to 65 except for using a Y type oxotitanylphthalocyanine (CG2-2) as the electric charge generating material, multi-layer type photosensitive materials for digital light source were produced, respectively.

Comparative Examples 10 to 12

According to the same manner as that described in Examples 61, 66 and 71 except for using a stilbene derivative (6-1) as the hole transferring material, multi-layer type photosensitive materials for digital light source were produced, respectively.

The photosensitive materials obtained in Examples 61 to 75 and Comparative Examples 10 to 12 were subjected to the following electrical characteristics test (II) and the electrical characteristics of the respective photosensitive materials were evaluated.

Electrical Characteristics Test (II)

According to the same manner as that described in the above electrical characteristics test (I) except for charging the surface of the photosensitive material to −700±20 V, the surface potential $V_0$ (V), residual potential $V_r$ (V) and half-life exposure $E_{1/2}$ (μJ/cm$^2$) were determined.

The kind of the electric charge generating material and hole transferring material used in the above respective Examples and Comparative Examples as well as test results of the electrical characteristics are shown in Table 6.

TABLE 6

| | Electric charge generating material | Hole transferring material | $V_o$ | $V_r$ | $E_{1/2}$ |
|---|---|---|---|---|---|
| Example 61 | CG 1-1 | 11-2 | −700 | −129 | 0.61 |
| Example 62 | CG 1-1 | 11-6 | −701 | −129 | 0.60 |
| Example 63 | CG 1-1 | 11-7 | −702 | −130 | 0.61 |
| Example 64 | CG 1-1 | 12-3 | −702 | −132 | 0.62 |

TABLE 6-continued

| | Electric charge generating material | Hole transferring material | $V_o$ | $V_r$ | $E_{1/2}$ |
|---|---|---|---|---|---|
| Example 65 | CG 1-1 | 12-5 | −698 | −134 | 0.64 |
| Example 66 | CG 2-1 | 11-2 | −700 | −104 | 0.54 |
| Example 67 | CG 2-1 | 11-6 | −702 | −101 | 0.52 |
| Example 68 | CG 2-1 | 11-7 | −701 | −103 | 0.54 |
| Example 69 | CG 2-1 | 12-3 | −698 | −107 | 0.55 |
| Example 70 | CG 2-1 | 12-5 | −699 | −105 | 0.54 |
| Example 71 | CG 2-2 | 11-2 | −706 | −94 | 0.39 |
| Example 72 | CG 2-2 | 11-6 | −702 | −96 | 0.40 |
| Example 73 | CG 2-2 | 11-7 | −703 | −93 | 0.38 |
| Example 74 | CG 2-2 | 12-3 | −700 | −100 | 0.41 |
| Example 75 | CG 2-2 | 12-5 | −701 | −99 | 0.40 |
| Comp. Ex. 10 | CG 1-1 | 6-1 | −700 | −158 | 0.75 |
| Comp. Ex. 11 | CG 2-1 | 6-1 | −698 | −163 | 0.79 |
| Comp. Ex. 12 | CG 2-2 | 6-1 | −703 | −162 | 0.79 |

(Single-layer type photosensitive material for analogue light source)

Examples 76 to 80

According to the same manner as that described in Examples 1 to 5 except for using a perylene pigment represented by the formula (CG3-1):

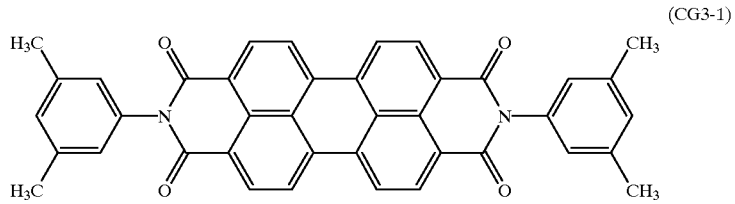

(CG3-1)

as the electric charge generating material, single-layer type photosensitive materials for analogue light source were produced.

Examples 81 to 85

According to the same manner as that described in Examples 6 to 10 except for using a perylene pigment (CG3-1) as the electric charge generating material, single-layer type photosensitive materials for analogue light source were produced, respectively.

Examples 86 to 90

According to the same manner as that described in Examples 11 to 15 except for using a perylene pigment (CG3-1) as the electric charge generating material, single-layer type photosensitive materials for analogue light source were produced, respectively.

Examples 91 to 95

According to the same manner as that described in Examples 15 to 20 except for using a perylene pigment (CG3-1) as the electric charge generating material, single-layer type photosensitive materials for analogue light source were produced, respectively.

Comparative Examples 13 to 15

According to the same manner as that described in Comparative Examples 1 to 3 except for using a perylene pigment (CG3-1) as the electric charge generating material, single-layer type photosensitive materials for analogue light source were produced.

The photosensitive materials obtained in Examples 76 to 95 and Comparative Examples 13 to 15 were subjected to the following electrical characteristics test (III) and the electrical characteristics of the respective photosensitive materials were evaluated, respectively.

Electrical Characteristics Test (III)

According to the same manner as that described in the above electrical characteristics test (I) except for using white light (light intensity: 8 lux) from a halogen lamp as an exposure light source, the surface potential $V_o$ (V), residual potential $V_r$ (V) and half-life exposure $E_{1/2}$ (lux·sec.) were determined.

The kind of the electric charge generating material, hole transferring material and electron transferring material used in the above respective Examples and Comparative Examples as well as test results of the electrical characteristics are shown in Table 7.

TABLE 7

| | Electric charge generating material | Hole trans- ferring material | Electron trans- ferring material | $V_o$ | $V_r$ | $E_{1/2}$ |
|---|---|---|---|---|---|---|
| Example 76 | CG 3-1 | 11-2 | — | 700 | 206 | 1.57 |
| Example 77 | CG 3-1 | 11-6 | — | 701 | 209 | 1.58 |
| Example 78 | CG 3-1 | 11-7 | — | 704 | 209 | 1.57 |
| Example 79 | CG 3-1 | 12-3 | — | 699 | 214 | 1.59 |
| Example 80 | CG 3-1 | 12-5 | — | 698 | 219 | 1.61 |
| Example 81 | CG 3-1 | 11-2 | ET17-1 | 704 | 182 | 1.47 |
| Example 82 | CG 3-1 | 11-6 | ET17-1 | 706 | 185 | 1.48 |
| Example 83 | CG 3-1 | 11-7 | ET17-1 | 700 | 185 | 1.48 |
| Example 84 | CG 3-1 | 12-3 | ET17-1 | 701 | 192 | 1.52 |
| Example 85 | CG 3-1 | 12-5 | ET17-1 | 704 | 191 | 1.52 |
| Example 86 | CG 3-1 | 11-2 | ET14-1 | 703 | 178 | 1.46 |
| Example 87 | CG 3-1 | 11-6 | ET14-1 | 699 | 178 | 1.46 |
| Example 88 | CG 3-1 | 11-7 | ET14-1 | 699 | 180 | 1.47 |
| Example 89 | CG 3-1 | 12-3 | ET14-1 | 700 | 188 | 1.50 |
| Example 90 | CG 3-1 | 12-5 | ET14-1 | 703 | 184 | 1.48 |
| Example 91 | CG 3-1 | 11-2 | ET14-2 | 702 | 171 | 1.43 |
| Example 92 | CG 3-1 | 11-6 | ET14-2 | 702 | 174 | 1.44 |
| Example 93 | CG 3-1 | 11-7 | ET14-2 | 700 | 171 | 1.42 |
| Example 94 | CG 3-1 | 12-3 | ET14-2 | 706 | 176 | 1.45 |
| Example 95 | CG 3-1 | 12-5 | ET14-2 | 704 | 177 | 1.45 |
| Comp. Ex. 13 | CG 3-1 | 6-1 | — | 695 | 235 | 1.75 |

TABLE 7-continued

| Electric charge generating material | Hole transferring material | Electron transferring material | $v_o$ | $v_r$ | $E_{1/2}$ |
| --- | --- | --- | --- | --- | --- |
| Comp. Ex. 14 | CG 3-1 | 6-2 | — | 704 | 240 | 1.79 |
| Comp. Ex. 15 | CG 3-1 | 6-3 | — | 703 | 239 | 1.79 |

Examples 96 to 100

According to the same manner as that described in Examples 76 to 80 except for using a bisazo pigment represented by the formula (CG4-1):

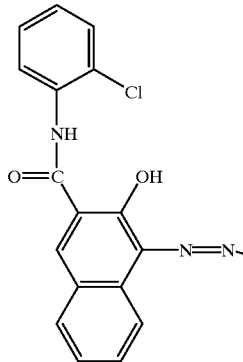
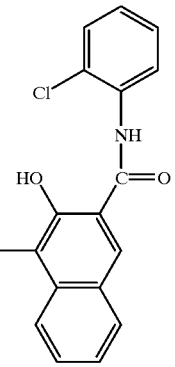
(CG4-1)

as the electric charge generating material, single-layer type photosensitive materials for analogue light source were produced, respectively.

Examples 101 to 105

According to the same manner as that described in Examples 81 to 85 except for using a bisazo pigment (CG4-1) as the electric charge generating material, single-layer type photosensitive materials for analogue light source were produced, respectively.

Examples 106 to 110

According to the same manner as that described in Examples 86 to 90 except for using a bisazo pigment (CG4-1) as the electric charge generating material, single-layer type photosensitive materials for analogue light source were produced, respectively.

Examples 111 to 115

According to the same manner as that described in Examples 91 to 95 except for using a bisazo pigment (CG4-1) as the electric charge generating material, single-layer type photosensitive materials for analogue light source were produced, respectively.

Comparative Examples 16 to 18

According to the same manner as that described in Comparative Examples 13 to 15 except for using a bisazo pigment (CG4-1) as the electric charge generating material, single-layer type photosensitive materials for analogue light source were produced, respectively.

The photosensitive materials obtained in Examples 96 to 115 and Comparative Examples 16 to 18 were subjected to the above electrical characteristics test (III) and the electrical characteristics of the respective photosensitive materials were evaluated. The kind of the electric charge generating material, hole transferring material and electron transferring material used in the above respective Examples and Comparative Examples as well as test results of the electrical characteristics are shown in Table 8.

TABLE 8

| | Electric charge generating material | Hole transferring material | Electron transferring material | $v_o$ | $v_r$ | $E_{1/2}$ |
| --- | --- | --- | --- | --- | --- | --- |
| Example 96 | CG 4-1 | 11-2 | — | 700 | 177 | 1.50 |
| Example 97 | CG 4-1 | 11-6 | — | 701 | 180 | 1.52 |
| Example 98 | CG 4-1 | 11-7 | — | 704 | 179 | 1.50 |
| Example 99 | CG 4-1 | 12-3 | — | 705 | 185 | 1.53 |
| Example 100 | CG 4-1 | 12-5 | — | 698 | 186 | 1.54 |
| Example 101 | CG 4-1 | 11-2 | ET17-1 | 699 | 149 | 1.33 |
| Example 102 | CG 4-1 | 11-6 | ET17-1 | 699 | 150 | 1.34 |
| Example 103 | CG 4-1 | 11-7 | ET17-1 | 700 | 149 | 1.34 |
| Example 104 | CG 4-1 | 12-3 | ET17-1 | 701 | 156 | 1.36 |
| Example 105 | CG 4-1 | 12-5 | ET17-1 | 702 | 155 | 1.36 |
| Example 106 | CG 4-1 | 11-2 | ET14-1 | 700 | 150 | 1.34 |
| Example 107 | CG 4-1 | 11-6 | ET14-1 | 704 | 149 | 1.34 |
| Example 108 | CG 4-1 | 11-7 | ET14-1 | 702 | 149 | 1.33 |
| Example 109 | CG 4-1 | 12-3 | ET14-1 | 705 | 158 | 1.37 |
| Example 110 | CG 4-1 | 12-5 | ET14-1 | 706 | 153 | 1.35 |
| Example 111 | CG 4-1 | 11-2 | ET14-2 | 700 | 138 | 1.29 |
| Example 112 | CG 4-1 | 11-6 | ET14-2 | 699 | 140 | 1.30 |
| Example 113 | CG 4-1 | 11-7 | ET14-2 | 698 | 140 | 1.31 |
| Example 114 | CG 4-1 | 12-3 | ET14-2 | 699 | 146 | 1.32 |
| Example 115 | CG 4-1 | 12-5 | ET14-2 | 704 | 148 | 1.34 |
| Comp. Ex. 16 | CG 4-1 | 6-1 | — | 695 | 200 | 1.59 |
| Comp. Ex. 17 | CG 4-1 | 6-2 | — | 699 | 199 | 1.59 |
| Comp. Ex. 18 | CG 4-1 | 6-3 | — | 703 | 195 | 1.58 |

Examples 116 to 120

According to the same manner as that described in Examples 76 to 80 except for using a bisazo pigment represented by the formula (CG4-2):

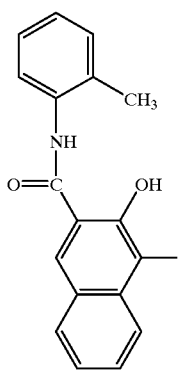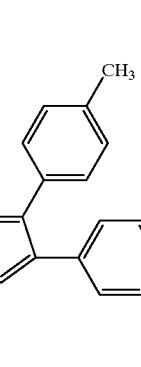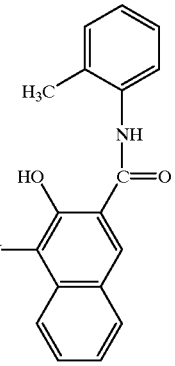

(CG4-2)

as the electric charge generating material, single-layer type photosensitive materials for analogue light source were produced, respectively.

Examples 121 to 125

According to the same manner as that described in Examples 81 to 85 except for using a bisazo pigment (CG4-2) as the electric charge generating material, single-layer type photosensitive materials for analogue light source were produced, respectively.

Examples 126 to 130

According to the same manner as that described in Examples 86 to 90 except for using a bisazo pigment (CG4-2) as the electric charge generating material, single-layer type photosensitive materials for analogue light source were produced, respectively.

Examples 131 to 135

According to the same manner as that described in Examples 91 to 95 except for using a bisazo pigment (CG4-2) as the electric charge generating material, single-layer type photosensitive materials for analogue light source were produced, respectively.

Comparative Examples 19 to 21

According to the same manner as that described in Comparative Examples 13 to 15 except for using a bisazo pigment (CG4-2) as the electric charge generating material, single-layer type photosensitive materials for analogue light source were produced, respectively.

The photosensitive materials obtained in Examples 116 to 135 and Comparative Examples 19 to 21 were subjected to the above electrical characteristics test (III) and the electrical characteristics of the respective photosensitive materials were evaluated. The kind of the electric charge generating material, hole transferring material and electron transferring material used in the above respective Examples and Comparative Examples as well as test results of the electrical characteristics are shown in Table 9.

TABLE 9

| | Electric charge generating material | Hole transferring material | Electron transferring material | $V_o$ | $V_r$ | $E_{1/2}$ |
|---|---|---|---|---|---|---|
| Example 116 | CG 4-2 | 11-2 | — | 706 | 203 | 1.61 |
| Example 117 | CG 4-2 | 11-6 | — | 700 | 204 | 1.61 |
| Example 118 | CG 4-2 | 11-7 | — | 698 | 202 | 1.61 |
| Example 119 | CG 4-2 | 12-3 | — | 699 | 207 | 1.63 |
| Example 120 | CG 4-2 | 12-5 | — | 699 | 208 | 1.63 |
| Example 121 | CG 4-2 | 11-2 | ET17-1 | 700 | 179 | 1.51 |
| Example 122 | CG 4-2 | 11-6 | ET17-1 | 701 | 181 | 1.52 |
| Example 123 | CG 4-2 | 11-7 | ET17-1 | 700 | 178 | 1.50 |
| Example 124 | CG 4-2 | 12-3 | ET17-1 | 697 | 185 | 1.53 |
| Example 125 | CG 4-2 | 12-5 | ET17-1 | 703 | 182 | 1.51 |
| Example 126 | CG 4-2 | 11-2 | ET14-1 | 704 | 166 | 1.40 |
| Example 127 | CG 4-2 | 11-6 | ET14-1 | 699 | 169 | 1.42 |
| Example 128 | CG 4-2 | 11-7 | ET14-1 | 705 | 167 | 1.41 |
| Example 129 | CG 4-2 | 12-3 | ET14-1 | 704 | 174 | 1.48 |
| Example 130 | CG 4-2 | 12-5 | ET14-1 | 702 | 172 | 1.46 |
| Example 131 | CG 4-2 | 11-2 | ET14-2 | 700 | 155 | 1.36 |
| Example 132 | CG 4-2 | 11-6 | ET14-2 | 701 | 156 | 1.37 |
| Example 133 | CG 4-2 | 11-7 | ET14-2 | 699 | 154 | 1.36 |
| Example 134 | CG 4-2 | 12-3 | ET14-2 | 697 | 160 | 1.39 |
| Example 135 | CG 4-2 | 12-5 | ET14-2 | 699 | 161 | 1.39 |
| Comp. Ex. 19 | CG 4-2 | 6-1 | — | 701 | 225 | 1.72 |
| Comp. Ex. 20 | CG 4-2 | 6-2 | — | 712 | 230 | 1.75 |
| Comp. Ex. 21 | CG 4-2 | 6-3 | — | 703 | 232 | 1.78 |

Examples 136 to 140

According to the same manner as that described in Examples 76 to 80 except for using a bisazo pigment represented by the formula (CG4-3):

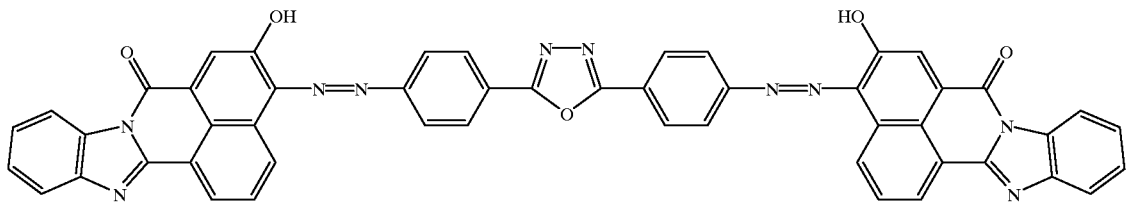
(CG4-3)

as the electric charge generating material, single-layer type photosensitive materials for analogue light source were produced, respectively.

Examples 141 to 145

According to the same manner as that described in Examples 81 to 85 except for using a bisazo pigment (CG4-3) as the electric charge generating material, single-layer type photosensitive materials for analogue light source were produced, respectively.

Examples 146 to 150

According to the same manner as that described in Examples 86 to 90 except for using a bisazo pigment (CG4-3) as the electric charge generating material, single-layer type photosensitive materials for analogue light source were produced, respectively.

Examples 151 to 155

According to the same manner as that described in Examples 91 to 95 except for using a bisazo pigment (CG4-3) as the electric charge generating material, single-layer type photosensitive materials for analogue light source were produced, respectively.

Comparative Examples 22 to 24

According to the same manner as that described in Comparative Examples 13 to 15 except for using a bisazo pigment (CG4-3) as the electric charge generating material, single-layer type photosensitive materials for analogue light source were produced, respectively.

The photosensitive materials obtained in Examples 136 to 155 and Comparative Examples 22 to 24 were subjected to the above electrical characteristics test (III) and the electrical characteristics of the respective photosensitive materials were evaluated. The kind of the electric charge generating material, hole transferring material and electron transferring material used in the above respective Examples and Comparative Examples as well as test results of the electrical characteristics are shown in Table 10.

TABLE 10

| | Electric charge generating material | Hole trans- ferring material | Electron trans- ferring material | $V_o$ | $V_r$ | $E_{½}$ |
|---|---|---|---|---|---|---|
| Example 136 | CG 4-3 | 11-2 | — | 704 | 204 | 1.61 |
| Example 137 | CG 4-3 | 11-6 | — | 700 | 204 | 1.61 |
| Example 138 | CG 4-3 | 11-7 | — | 702 | 202 | 1.60 |
| Example 139 | CG 4-3 | 12-3 | — | 706 | 207 | 1.63 |
| Example 140 | CG 4-3 | 12-5 | — | 703 | 208 | 1.63 |

TABLE 10-continued

| | Electric charge generating material | Hole trans- ferring material | Electron trans- ferring material | $V_o$ | $V_r$ | $E_{½}$ |
|---|---|---|---|---|---|---|
| Example 141 | CG 4-3 | 11-2 | ET17-1 | 700 | 179 | 1.48 |
| Example 142 | CG 4-3 | 11-6 | ET17-1 | 698 | 181 | 1.48 |
| Example 143 | CG 4-3 | 11-7 | ET17-1 | 697 | 180 | 1.47 |
| Example 144 | CG 4-3 | 12-3 | ET17-1 | 697 | 185 | 1.49 |
| Example 145 | CG 4-3 | 12-5 | ET17-1 | 702 | 184 | 1.49 |
| Example 146 | CG 4-3 | 11-2 | ET14-1 | 701 | 181 | 1.48 |
| Example 147 | CG 4-3 | 11-6 | ET14-1 | 699 | 183 | 1.49 |
| Example 148 | CG 4-3 | 11-7 | ET14-1 | 704 | 182 | 1.49 |
| Example 149 | CG 4-3 | 12-3 | ET14-1 | 703 | 186 | 1.50 |
| Example 150 | CG 4-3 | 12-5 | ET14-1 | 701 | 186 | 1.50 |
| Example 151 | CG 4-3 | 11-2 | ET14-2 | 704 | 176 | 1.47 |
| Example 152 | CG 4-3 | 11-6 | ET14-2 | 698 | 180 | 1.48 |
| Example 153 | CG 4-3 | 11-7 | ET14-2 | 702 | 179 | 1.47 |
| Example 154 | CG 4-3 | 12-3 | ET14-2 | 699 | 184 | 1.49 |
| Example 155 | CG 4-3 | 12-5 | ET14-2 | 698 | 183 | 1.50 |
| Comp. Ex. 22 | CG 4-3 | 6-1 | — | 712 | 225 | 1.72 |
| Comp. Ex. 23 | CG 4-3 | 6-2 | — | 713 | 230 | 1.75 |
| Comp. Ex. 24 | CG 4-3 | 6-3 | — | 719 | 229 | 1.73 |

(Multi-layer type photosensitive material for analogue light source)

Examples 156 to 160

According to the same manner as that described in Examples 61 to 65 except for using a perylene pigment (CG3-1) as the electric charge generating material, multi-layer type photosensitive materials for analogue light source were produced, respectively.

Examples 161 to 165

According to the same manner as that described in Examples 61 to 65 except for using a perylene pigment (CG4-1) as the electric charge generating material, multi-layer type photosensitive materials for analogue light source were produced, respectively.

Examples 166 to 170

According to the same manner as that described in Examples 61 to 65 except for using a perylene pigment (CG4-2) as the electric charge generating material, multi-layer type photosensitive materials for analogue light source were produced, respectively.

Examples 171 to 175

According to the same manner as that described in Examples 61 to 65 except for using a perylene pigment (CG4-3) as the electric charge generating material, multi-layer type photosensitive materials for analogue light source were produced, respectively.

Comparative Examples 25 to 28

According to the same manner as that described in Examples 156, 161, 166 and 171 except for using a stilbene derivative (6-1) as the hole transferring material, multi-layer type photosensitive materials for analogue light source were produced, respectively.

The photosensitive materials obtained in Examples 156 to 175 and Comparative Examples 25 to 28 were subjected to the following electrical characteristics test (IV) and the electrical characteristics of the respective photosensitive materials were evaluated.

Electrical Characteristics Test (IV)

According to the same manner as that described in the above electrical characteristics test (III) except for charging the surface of the photosensitive material to $-700\pm20$ V, the surface potential $V_0$ (V), residual potential $V_r$ (V) and half-life exposure $E_{1/2}$ (lux·sec.) were determined.

The kind of the electric charge generating material and hole transferring material used in the above respective Examples and Comparative Examples as well as test results of the electrical characteristics are shown in Table 11.

TABLE 11

| | Electric charge generating material | Hole transferring material | $V_o$ | $V_r$ | $E_{1/2}$ |
|---|---|---|---|---|---|
| Example 156 | CG 3-1 | 11-2 | −701 | −125 | 1.89 |
| Example 157 | CG 3-1 | 11-6 | −702 | −129 | 1.91 |
| Example 158 | CG 3-1 | 11-7 | −698 | −125 | 1.90 |
| Example 159 | CG 3-1 | 12-3 | −700 | −136 | 1.94 |
| Example 160 | CG 3-1 | 12-5 | −704 | −134 | 1.93 |
| Example 161 | CG 4-1 | 11-2 | −701 | −108 | 1.79 |
| Example 162 | CG 4-1 | 11-6 | −705 | −106 | 1.80 |
| Example 163 | CG 4-1 | 11-7 | −704 | −108 | 1.80 |
| Example 164 | CG 4-1 | 12-3 | −700 | −121 | 1.86 |
| Example 165 | CG 4-1 | 12-5 | −704 | −119 | 1.85 |
| Example 166 | CG 4-2 | 11-2 | −703 | −120 | 1.86 |
| Example 167 | CG 4-2 | 11-6 | −698 | −124 | 1.87 |
| Example 168 | CG 4-2 | 11-7 | −699 | −122 | 1.86 |
| Example 169 | CG 4-2 | 12-3 | −706 | −128 | 1.88 |
| Example 170 | CG 4-2 | 12-5 | −702 | −126 | 1.88 |
| Example 171 | CG 4-3 | 11-2 | −701 | −102 | 1.77 |
| Example 172 | CG 4-3 | 11-6 | −704 | −106 | 1.78 |
| Example 173 | CG 4-3 | 11-7 | −705 | −103 | 1.77 |
| Example 174 | CG 4-3 | 12-3 | −700 | −109 | 1.80 |
| Example 175 | CG 2-2 | 12-5 | −697 | −111 | 1.81 |
| Comp. Ex. 25 | CG 3-1 | 6-1 | −706 | −158 | 2.01 |
| Comp. Ex. 26 | CG 4-1 | 6-1 | −703 | −163 | 2.11 |
| Comp. Ex. 27 | CG 4-2 | 6-1 | −709 | −152 | 2.00 |
| Comp. Ex. 28 | CG 4-3 | 6-1 | −700 | −163 | 2.09 |

As is apparent from Tables 3 to 11, the electrophotosensitive materials of Examples 1 to 175 show small absolute value of the residual potential $V_r$ in comparison with the Comparative Examples corresponding to the respective Examples. With respect to the half-life exposure $E_{1/2}$, respective value in the Examples is the same as or smaller than that of the corresponding Comparative Examples. Consequently, it is found that the electrophotosensitive materials of Examples 1 to 175 have excellent sensitivity.

According to the same manner as that described in Examples 1–175, electrophotosensitive materials (single-layer type or multi-layer type photoconductor for analogue-light source, or single-layer type or multi-layer type photoconductor for digital-light source can be produced by using the stilbene derivative (11-14) to (11-18) of Synthesis Examples 6–10 or the stilbene derivative (12-14) to (12-18) of Synthesis Examples 11–15, which show an excellent sensitivity similar to electrophotosensitive materials of Examples 1–175.

What is claimed is:

1. A stilbene derivative represented by the general formula (1):

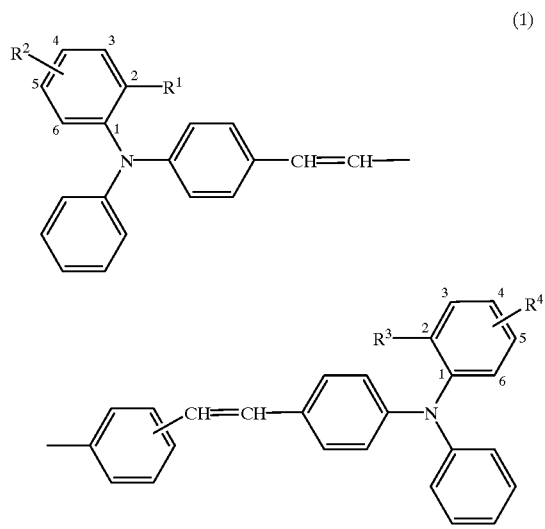

wherein $R^1$ and $R^3$ are the same or different and represent an alkyl group, an aryl group, aralkyl group or an alkoxy group which are optionally substituted; and $R^2$ and $R^4$ are the same or different and represent a hydrogen atom, an alkyl group or an alkoxy group which are optionally substituted, provided that (1) when the substitution position of $R^2$ and $R^4$ is the 4 (para)-position, $R^2$ and $R^4$ are hydrogen atoms, and (2) when both of $R^1$ and $R^3$ are methyl groups, $R^2$ and $R^4$ are the same or different and represent an alkyl group or an alkoxy group which are optionally substituted.

2. The stilbene derivative according to claim 1, wherein $R^3$ and $R^1$ in the general formula (1) are the same groups and $R^4$ and $R^2$ are the same groups.

3. The stilbene derivative according to claim 1, wherein the compound represented by the general formula (1) is a compound represented by the following general formula (1)-1:

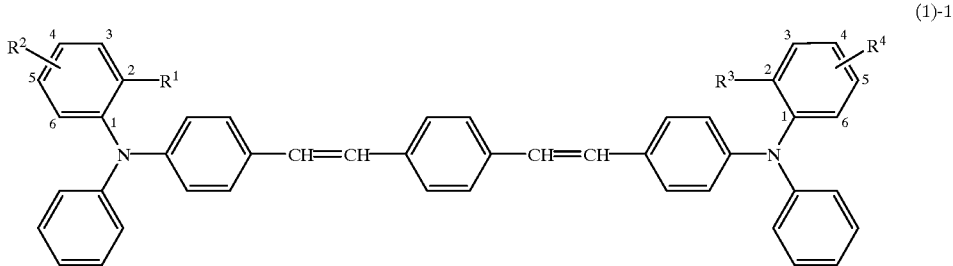

wherein $R^1$ and $R^3$ are the same or different and represent an alkyl group, an aryl group, an aralkyl group or an alkoxy group which are optionally substituted; and $R^2$ and $R^4$ are the same or different and represent a hydrogen atom, an alkyl group or an alkoxy group which are optionally substituted, provided that when the substitution position of $R^2$ and $R^4$ is the 4-(para) position, $R^2$ and $R^4$ are hydrogen atoms.

4. The stilbene derivative according to claim 1, wherein the compound represented by the general formula (1) is a compound represented by the following general formula (1)-2:

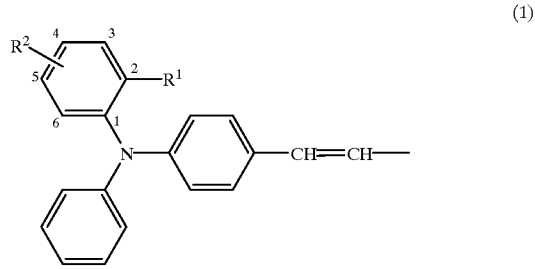

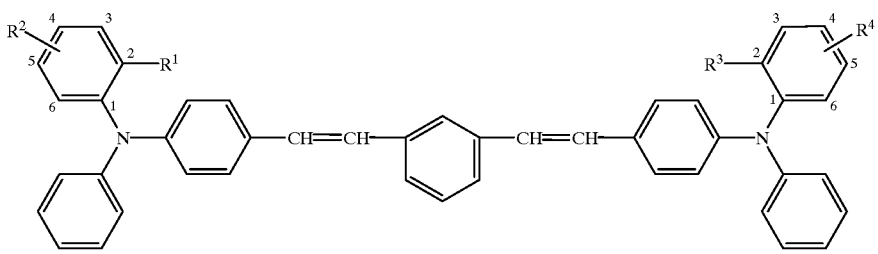

wherein $R^1$ and $R^3$ are the same or different and represent an alkyl group, an aryl group, an aralkyl group or an alkoxy group which are optionally substituted; and $R^2$ and $R^4$ are the same or different and represent a hydrogen atom, an alkyl group or an alkoxy group which are optionally substituted, provided that when (1) the substitution position of $R^2$ and $R^4$ is the 4 (para)-position, $R^2$ and $R^4$ are hydrogen atoms, and (2) when both of $R^1$ and $R^3$ are methyl groups, $R^2$ and $R^4$ are the same or different and represent an alkyl group or an alkoxy group which are optionally substituted.

5. A stilbene derivative represented by the general formula (1):

-continued

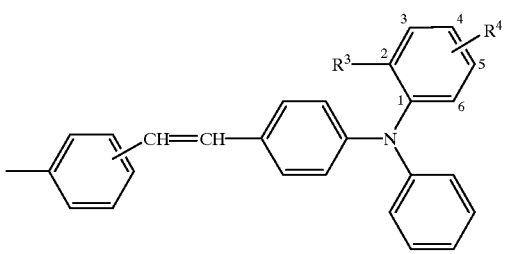

wherein $R^1$ and $R^3$ are the same or different and represent an alkyl group having 1 to 6 carbon atoms, an aryl group selected from the group consisting of phenyl, naphtyl, anthoryl and penanthoryl, an aralkyl group having 1 to 6 carbon atoms in the alkyl moiety or an alkoxy group having 1 to 6 carbon atoms, the groups of which are optionally substituted; and R² and R⁴ are the same or different and represent an alkyl group having 1 to 6 carbon atoms or an alkoxy group having 1 to 6 carbon atoms, the groups of which are optionally substituted.

6. The stilbene derivative according to claim 5, wherein the compound represented by the general formula (1) is a compound represented by the general formula (1)-1

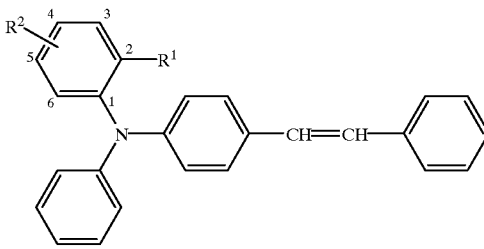
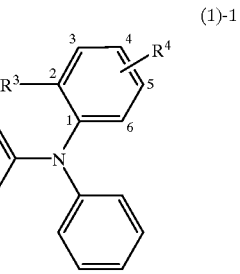

(1)-1 wherein R¹ and R³ are the same or different and represent an alkyl group having 1 to 6 carbon atoms, an aryl group selected from the group consisting of phenyl naphtyl, anthoryl and phenanthoryl, an aralkyl group having 1 to 6 carbon atoms in the alkyl moiety or an alkoxy group having 1 to 6 carbon atoms, the groups of which are optionally substituted; and R² and R⁴ are the same or different and represent an alkyl group having 1 to 6 carbon atoms or an alkoxy group having 1 to 6 carbon atoms, the groups of which are optionally substituted.

7. The stilbene derivative according to claim 6, wherein R¹ is a methyl group, R² is a methyl group at the 6-position, R³ is a methyl group and R⁴ is a methyl group at the 6-position.

8. The stilbene derivative according to claim 6, wherein R¹ is a methyl group, R² is a methyl group at the 3-position, R³ is a methyl group and R⁴ is a methyl group at the 3-position.

9. The stilbene derivative according to claim 6, wherein R¹ is a methyl group, R² is a methyl group at the 5-position, R³ is a methyl group and R⁴ is a methyl group at the 5-position.

10. The stilbene derivative according to claim 6, wherein R¹ is an ethyl group, R² is a methyl group at the 6-position, R³ is an ethyl group and R⁴ is a methyl group at the 6-position.

11. The stilbene derivative according to claim 6, wherein R¹ is an ethyl group, R² is an ethyl group at the 6-position, R³ is an ethyl group and R⁴ is an ethyl group at the 6-position.

12. The stilbene derivative according to claim 6, wherein R¹ is a isopropyl group, R² is a methyl group at the 6-position, R³ is an isopropyl group and R⁴ is a methyl group at the 6-position.

13. The stilbene derivative according to claim 6, wherein R¹ is a tert-butyl group, R² is a tert-butyl group at the 5-position, R³ is a tert-butyl group and R⁴ is a tert-butyl group at the 5-position.

14. The stilbene derivative according to claim 6, wherein R¹ is a methoxy group, R² is a methyl group at the 6-position, R³ is a methoxy group and R⁴ is a methyl group at the 6-position.

15. The stilbene derivative according to claim 5, wherein the compound represented by the general formula (1) is a compound represented by the general formula (1)-2:

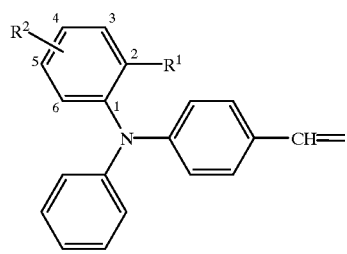

(1)-2 wherein R¹ and R³ are the same or different and represent an alkyl group having 1 to 6 carbon atoms, an aryl group selected from the group consisting of phenyl, naphtyl, anthoryl and phenanthoryl, and aralkyl group having 1 to 6 carbon atoms in the alkyl moiety or an alkoxy group having 1 to 6 carbon atoms, the groups of which are optionally substituted; and R² and R⁴ are the same or different and represent an alkyl group having 1 to 6 carbon atoms or an alkoxy group having 1 to 6 carbon atoms, the groups of which are optionally substituted.

16. The stilbene derivative according to claim 15, wherein R¹ is a methyl group, R² is a methyl group at the 6-position, R³ is a methyl group and R⁴ is a methyl group at the 6-position.

17. The stilbene derivative according to claim 15, wherein R¹ is a methyl group, R² is a methyl group at the 3-position, R³ is a methyl group and R⁴ is a methyl group at the 3-position.

18. The stilbene derivative according to claim 15, wherein $R^1$ is a methyl group, $R^2$ is a methyl group at the 5-position, $R^3$ is a methyl group and $R^4$ is a methyl group at the 5-position.

19. The stilbene derivative according to claim 15, wherein $R^1$ is an ethyl group, $R^2$ is a methyl group at the 6-position, $R^3$ is an ethyl group and $R^4$ is a methyl group at the 6-position.

20. The stilbene derivative according to claim 15, wherein $R^1$ is an ethyl group, $R^2$ is a ethyl group at the 6-position, $R^3$ is a ethyl group and $R^4$ is a ethyl group at the 6-position.

21. The stilbene derivative according to claim 15, wherein $R^1$ is an isopropyl group, $R^2$ is a methyl group at the 6-position, $R^3$ is an isopropyl group and $R^4$ is a methyl group at the 6-position.

22. The stilbene derivative according to claim 15, wherein $R^1$ is a tert-butyl group, $R^2$ is a tert-butyl group at the 5-position, $R^3$ is a tert-butyl group and $R^4$ is a tert-butyl group at the 5-position.

23. The stilbene derivative according to claim 15, wherein $R^1$ is a methoxy group, $R^2$ is a methyl group at the 6-position, $R^3$ is a methoxy group and $R^4$ is a methyl group at the 6-position.

24. The stilbene derivative according to claim 15, wherein $R^1$ is a methoxy group, $R^2$ is a methyl group at the 5-position, $R^3$ is a methoxy group and $R^4$ is a methyl group at the 5-position.

25. The stilbene derivative according to claim 15, wherein $R^1$ is a methyl group, $R^2$ is a methoxy group at the 5-position, $R^3$ is a methyl group and $R^4$ is a methoxy group at the 5-position.

26. The stilbene derivative according to claim 5, wherein $R^2$ and $R^4$ are substituted in the 3-, 5-, or 6-position.

27. A method for producing a stilbene derivative represented by the general formula (1):

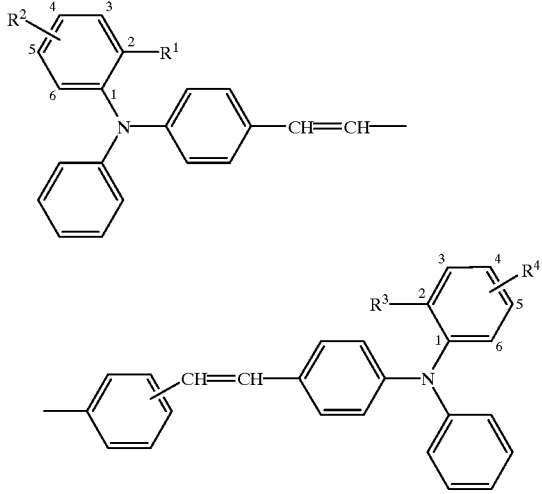

wherein $R^1$ and $R^3$ are the same or different and represent an alkyl group, an aryl group, aralkyl group or an alkoxy group which are optionally substituted; and $R^2$ and $R^4$ are the same or different and represent a hydrogen atom, an alkyl group or an alkoxy group which are optionally substituted, provided that when the substitution position of $R^2$ and are the same groups, which comprises reacting a formulated triphenylamine derivative represented by the general formula (2):

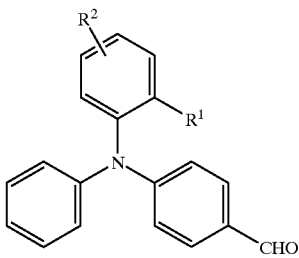

(wherein $R^1$ represents an alkyl group, an aryl group, an aralkyl group or an alkoxy group which are optionally substituted; and $R^2$ represents a hydrogen atom, an alkyl group or an alkoxy group which are optionally substituted, provided that when the substitution position of $R^2$ is the 4(para) position, $R^2$ is a hydrogen atom) with a bisphosphate derivative represented by the general formula (3):

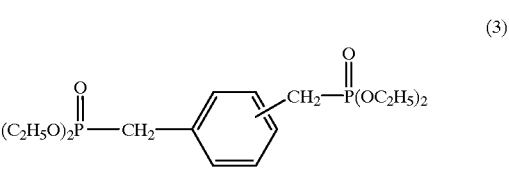

28. The method for producing the stilbene derivative according to claim 5, the formulated triphenylamine derivative (2) is obtained by reacting an aniline derivative represented by the general formula (4):

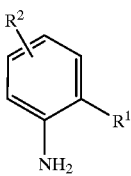

(wherein $R^1$ and $R^2$ are as defined above) with iodobenzene to obtain a triphenylamine derivative represented by the general formula (5):

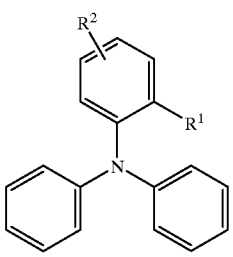

(wherein $R^1$ and $R^2$ are as defined above) and formylating this compound (5) by the Vilsmeier method.

29. An electrophotosensitive material comprising a conductive substrate and a photosensitive layer provided on the conductive substrate, wherein said photosensitive layer contains a stilbene derivative of claim 1.

30. The electrophotosensitive material according to claim 29, wherein said photosensitive layer contains an electric charge generating material and electric charge transferring material in combination with said stilbene derivative.

* * * * *